United States Patent [19]

Hall et al.

[11] Patent Number: 5,760,102
[45] Date of Patent: Jun. 2, 1998

[54] USES OF DENTURE ADHESIVE CONTAINING ALOE EXTRACT

[75] Inventors: John E. Hall; Kenneth M. Yates, both of Grand Prairie, Tex.

[73] Assignee: Carrington Laboratories, Inc., Irving, Tex.

[21] Appl. No.: 602,500

[22] Filed: Feb. 20, 1996

[51] Int. Cl.$^6$ .................................................. A61K 6/00
[52] U.S. Cl. .......................... 523/120; 524/27; 524/78; 433/180; 536/4.1; 536/123.1
[58] Field of Search ............... 523/120; 524/27, 524/78; 433/180; 536/4.1, 123.1

[56] References Cited

U.S. PATENT DOCUMENTS

| | | | |
|---|---|---|---|
| 3,440,065 | 4/1969 | La Via et al. | 106/35 |
| 4,465,517 | 8/1984 | Shields | 106/35 |
| 4,474,902 | 10/1984 | Dhabhar et al. | 523/120 |
| 4,572,832 | 2/1986 | Kigasawa et al. | 514/775 |
| 4,695,465 | 9/1987 | Kigasawa et al. | 424/15 |
| 4,804,412 | 2/1989 | Komiyama et al. | 106/35 |
| 4,894,323 | 1/1990 | Reül et al. | 424/439 |
| 5,001,170 | 3/1991 | Keegan | 523/120 |
| 5,006,571 | 4/1991 | Kumar et al. | 523/120 |
| 5,024,701 | 6/1991 | Desmarais | 106/35 |
| 5,093,387 | 3/1992 | Schobel et al. | 523/120 |
| 5,158,934 | 10/1992 | Ammann et al. | 514/900 |
| 5,286,764 | 2/1994 | Prosise | 523/120 |
| 5,302,628 | 4/1994 | Lim et al. | 523/105 |
| 5,369,145 | 11/1994 | Gasman et al. | 523/120 |
| 5,395,867 | 3/1995 | Prosise | 524/55 |
| 5,409,703 | 4/1995 | McAnalley et al. | 536/128 |

FOREIGN PATENT DOCUMENTS

| | | | |
|---|---|---|---|
| 1 147 352 | 4/1963 | Germany. | |
| WO 92/15289 | 9/1992 | WIPO | 9/70 |
| WO 95/00184 | 1/1995 | WIPO | 25/28 |

*Primary Examiner*—Andrew E. C. Merriam
*Attorney, Agent, or Firm*—Hitt Chwang & Gaines, P.C.

[57] ABSTRACT

A method of adhering a denture, having a biocontact surface, to a gum or a roof of a mouth, containing the steps of: (1) Treating the biocontact surface of the denture with a denture adhesive composition containing a chemical substance derived from an aloe leaf to obtain a treated denture; and (2) placing the treated denture in close proximity to a gum or the roof of the mouth thereby engaging the treated denture with the gum or the roof of the mouth. A method of preparing a denture adhesive composition containing a chemical substance derived from an aloe leaf.

33 Claims, 11 Drawing Sheets

USES OF DENTURE ADHESIVE CONTAINING ALOE EXTRACT

BACKGROUND

The present invention pertains to a denture adhesive, and more particularly, to the uses of a denture adhesive containing substances isolated or derived from an aloe vera leaf and its preparations. The substances can be concentrated gel from aloe, such as, aloe vera gel extract, bulk acetylated mannans or bulk pharmaceutical mannans, and acemannan, all of which can be isolated or derived from aloe gel fillet.

ALOE VERA

Aloe is a tropical or subtropical plant characterized by lance-shaped leaves with jagged edges and sharp points. For centuries, this plant has been considered to have, and has been used for its, medicinal and therapeutic properties without any clear understanding or scientific analysis of the bases for such properties. It is also known that the biological activities of fresh aloe plant decay very rapidly.

Because of this lack of knowledge about the aloe plant, most methods employed for the processing of the plant result in end products which vary widely. Further, aloe leaves contain anthraquinones in the yellow sap. The anthraquinone-containing yellow sap is known to have a laxative effect with a reputation as an extremely irritating cathartic. Traditional processes for the production of various aloe products typically involved crushing (pressure rollers), grinding (e.g., use of Thompson aloe leaf slitter), or pressing (TCX pressure extruder) of the entire leaf of the aloe plant to produce an aloe vera juice, followed by various steps of filtration and stabilization of the juice. The resulting mixture is then incorporated in, or mixed with, other solutions or agents to produce the products which could be, for example, a cosmetic, a health food drink, or a topical ointment. Unfortunately, because of improper processing procedures, many of these so-called aloe products contain no bioactive chemical substances or ingredients.

Further, unless carefully controlled processes are used in processing the leaves of the aloe plant, the active chemical substances, or ingredients, of the leaves are destroyed during the process.

Aloe vera leaves contain a variety of chemical substances and components. Mixtures of active chemical substances of aloe leaves have been identified, isolated and stabilized as described in U.S. Pat. Nos. 4,735,935, 4,851,224, 4,917,890, 4,957,907, 4,959,214, and 4,966,892, the content of each of these patents is incorporated herein by reference. One group of the active chemical substances has been referred to as aloe vera mucilaginous polysaccharides. Even the aloe vera mucilaginous polysaccharides are made up of a mixture of polysaccharides. The term "polysaccharides" has been used loosely to include both oligomers and polymers of carbohydrates. A group of such polysaccharides from aloe vera gel extract has been given the name acemannan. Acemannan is an ordered linear polymer of substantially acetylated mannose monomers.

The biological, or physiological, activities of aloe vera mucilaginous polysaccharides and their pharmaceutical applications have been the object of numerous research studies at a number of laboratories, including Carrington Laboratories. Uses of aloe products have been described in U.S. Pat. Nos. 5,106,616, 5,118,673, 5,308,838, 5,441,943, and 5,443,830, each assigned to Carrington Laboratories, Inc., the content of each of which is incorporated by reference herein. These studies have primarily focused on the activities of bioactive chemical substances of aloe vera as antiviral agents, antitumor agents, immunostimulants, immunomodulators, vaccine adjuvants, means of reducing opportunistic infections, means of controlling inflammation, and means of stimulating the wound healing processes.

Aloe vera mucilaginous polysaccharides have been shown in controlled studies to increase the rate of healing in animals. Aloe vera mucilaginous polysaccharides have also been shown to be an effective treatment for gastric ulcers in animal studies.

Acemannan, for example, has been shown in laboratory studies to increase up to 300% in 48 hours the replication of fibroblasts in tissue culture which are known to be responsible for healing burns, ulcers and other wounds of the skin and of the gastrointestinal lining.

DENTURE ADHESIVES

The concept of removable prosthodontics is now broadly accepted. Adjunctive devices such as denture adhesives are now widely used by the public.

Yankell, in an overview of denture adhesives, described the first patent pertaining to denture adhesives issued in 1913. S. L. Yankell, "Overview of Research and Literature on Denture Adhesives," *Compend Cont. Educat.*, suppl. 4, S18–S21, 1984. Other denture adhesive patents followed in the 1920's and 1930's. In the *Accepted Dental Remedies* of 1935, the Council of Dental Materials, Instruments, and Equipment of the American Dental Association, took the position that denture adhesives were not medicinal. The use of denture adhesives, in fact, was discouraged in that time. The negative attitude toward denture adhesives came, in part, from the idea that for well constructed dentures to function properly, neither adhesives nor other adjunctive devices should be required. F. H. McKevitt, "The Measured Vertical Dimension and Denture Adhesive Powders," *J. Prosth. Dent.* 1:393–401, 1950. The view is still being maintained. W. B. Love, et al., "Denture Adhesives-pH and Buffering Capacity," *J. Prosth. Dent.* 66:356–360, 1991.

Much of the negative attitude towards the use of denture adhesives has come from reports that most denture adhesives cause deleterious effects to denture patients. Denture adhesives have been blamed for the prolonged use of ill fitting dentures. Moreover, denture adhesives have been reported to increase vertical dimension of occlusion, to act as allergens or irritants, and to alter the oral microflora.

In the last five years, the general attitude of not using denture adhesives has changed. Studies have shown positive results of using denture adhesives. A minute amount of denture adhesive can improve denture retention, decrease discomfort, reduce the need of frequent adjustments, and even prevent strangulation of the mucosal blood supply. Denture adhesives have also been reported to reduce mucosal irritation from ill fitting dentures, reduce compression ulcers, and reduce patchy inflammation. In fact, patients having sensitive oral mucosa are those who can benefit most from the use of denture adhesives. The use of denture adhesives has been reported to: (1) Reduce the amount of food impaction under the denture base thus reduce the microbial load around the area; (2) improve chewing efficiency and bite force as a result of greater distribution of occlusal forces over the denture bearing tissues and as a result of reducing local pressure points; and (3) provide a cushioning or lubricating effect to reduce function and mucosal irritation. Highly viscous adhesive dentures that slowly leach from under the denture may prevent further dehydration of tissues in a xerostomic patient. Other patients who can benefit from using denture adhesives include those who suffer from a deficit in muscle control, such as hormonal or neurotransmitter changes, myasthenia gravis, muscular dystrophy, dyskinesias, Parkinsonian syndromes, or Alzheimer's disease. A denture adhesive can swell from about 50 to about 150% in volume of the original volume. This swelling of adhesive can occupy the void between the base of the denture and the supporting mucosa of the mouth. Water and saliva found in the void are displaced by the adhesive. The surface tension coefficient of the fluid film between the denture base and the supporting mucosa is increased by the presence of the denture adhesive. Water or saliva absorbed by the adhesive also contribute to the "stickiness" of the material.

On a personal basis, denture adhesives improve the confidence level of new denture wearers letting them have a better chance to adjust to eating and socializing in public.

Now, about 75% of all dentist are recommending their denture patients to use some kinds of denture adhesives with the dentures. Thus, millions of denture wearers are now using denture adhesives. It is estimated that about one sixth of denture wearers use denture adhesives more than eight times a week, about two-fifths of the denture wearers use the products about eight times a week, and the remaining patients used the products about four times a week.

For a denture adhesive to receive a designation of "Acceptance" by the American Dental Association Council, certain criteria must be met. The product must function as an adhesive, and must not affect the integrity of the denture, and must show biological acceptability. As of 1990, the products that have received a designation of "Acceptance" include those having the following trademarks or tradenames: Corga, Effergrip, Firmdent, Orafix, Permagrip paste and powder, Rigident paste and powder, Wernet's cream and powder, Super Wernet's Powder, Secure, and others.

Currently marketed denture adhesives come in the form of a powder, a paste or a solid film. They usually contain one or more ingredients that swell and become sticky and viscous upon absorbing water. Some examples of these ingredients include natural ingredients such as, Karaya gum, acacia gum, gelatin, pectin, tragacanth, methylcellulose, hydroxymethyl cellulose, and carboxymethyl cellulose. Usable synthetic polymers include polyethylene oxide, vinyl methyl ether/maleic anhydrides, cationic polyacrylamides, acetic polyvinyl compounds, and others. Mainly, these ingredients are either carbohydrates or some chemicals behaving like carbohydrates. G. Stafford, "Efficiency of Denture Adhesives and Their Possible Influence on Oral microorganisms," *J. Dent Res.* 50:832–836, 1971. Other ingredients found in the denture adhesives include: Coloring agents, flavoring agents, wetting agents, and preservatives. Commonly used preservatives are sodium borate, sodium tetraborate, hexachlorophene, and propylhydroxy benzoate. Thinning and binding agents that can also be added to the dental adhesives include polyethylene, mineral oil and petroleum products. To prevent clumping, the powder products can include magnesium iodide, sodium phosphate, or calcium silicate. B. Ellis, et al., "The composition and Rheology of Denture Adhesives," *J. Dent.* 8:109–118, 1980.

When first applied, a denture adhesive holds the denture very well. The adhesive absorbs water in the mouth and swells to form a continuous polymer matrix. Over time, however, saliva and other oral fluids start to disintegrate the polymer matrix, causing the adhesive to lose its viscosity, its "stickiness" and its bond strength. Most commercially available denture adhesives can retain their bonding abilities for about three to eight hours.

A desirable denture adhesive must be able to firmly adhere the denture in place when wanted. The ideal denture adhesive should retain its adhesiveness for from about 12 to about 16 hours. It should not be toxic, it should not irritate the supporting oral mucosa, and, preferably, it should provide comfort to the underlying oral mucosa. A denture adhesive should not cause an allergic reaction to the person using the adhesive. The absence of taste and odor would also be a plus. Further, a denture adhesive should be easy to apply and to remove. Moreover, the adhesive should possess a pH that would not cause tooth demineralization. The adhesive should not disturb the normal oral flora. Further, the denture adhesive should not cause damage to the denture materials or to any other dental restorative materials.

Unfortunately, all currently commercially available denture adhesives are far from ideal. Their inherent problems limit their use, compromise their effectiveness, or even cause harm to the denture wearers.

For example, many denture adhesives contain Karaya gum. Karaya gum is a common vegetable gum which is included in the composition of the denture adhesives to absorb water and to increase viscosity. Adhesives that contain Karaya gum have been known to cause allergic reactions to certain patients using the adhesives. The symptoms include hives, epigastric pain, nausea, angioneurotic edema, and even vomiting. W. J. Hogan, "Allergic Reaction to Denture Adhesive Powders," *N. Y. Dent. J.* 20:65–66, 1954; and K. D. Figely, "Karaya Gum Hypersensitivity," *JAMA* 114:747–748, 1940. Even worse, the manufacturing processes of some denture adhesives introduce microorganisms, which are rarely found in the mouth of a human, into the adhesives. G. Stafford, et al., "Efficiency of Denture Adhesives and Their Possible Influence on Oral Microorganisms," *J. Dent. Res.* 50:832–836, 1971. Many commercially available denture adhesives are shown to initiate and promote the growth of microbes in the mouth. W. D. Gates, et al., "Microbial Contamination in Four Commercially Available Denture Adhesives," *J. Prosth. Dent.* 71:154–158, 1994. It has been reported that micro flora can become imbalanced if certain microorganisms grow out of hand while the growth of others is inhibited. H. Bartels, "Bacteriological Appraisal of Denture Adhesive Powders," *J. Dent. Res.* 24:15–16, 1945. Nearly all of the commercially available denture adhesives have been shown to be cytotoxic to fibroblasts grown in cultures. B. Elkstrand, et al., "Denture Adhesives: Cytotoxicity, Microbial Contamination, and Formaldehyde Content," *J. Prosth. Dent.*, 69:314–317, 1993. Some of them are potent allergens, some of them even release formaldehyde into the oral cavity during use. S. L. Yankell, "Overview of Research and Literature on Denture Adhesives," *Compend Cont. Educat.* Suppl. 4, S18–S21, 1984. Formaldehyde is, of course, toxic and is an allergen. W. P. Jodan, et al., "Threshold Responses in Formaldehyde-Sensitive Subjects," *J. Am. Acad Dermatol.* 1:44–48, 1979. Almost all of the commercially available denture adhesives contain large amounts of sodium salts, preservative, and/or antimicrobial agents. The sodium can get into the system of the denture wearer by ingestion or absorption through chronic contact. Sodium, of course, is detrimental to people with hypertension, a special concern for geriatric denture wearers which make up a significant portion of the patients. M. E. Safar, et al., "Sodium, Large Arteries, and Diuretic Compounds in Hypertension," *Amer. J. Med. Scien.* 307 Suppl 1:S3–S8, 1994.

As mentioned above, many of the commercially available denture adhesives contain Karaya gum. Karaya gum forms an acidic solution in the mouth of the denture wearer.

Despite dilution in the oral cavity, these adhesives can create an acidic environment in the mouth for about 24 hours. The pH of the solution can drop to below 5.5. Hydroxyapatite structure will dissolve in a solution which has an acidity below the critical pH of about 5.5. G. N. Jenkins, *The Physiology and Biochemistry of the Mouth*, 4th Ed., London: Blackwell Scientific publications: 299, 1978. What makes the matter worse is that many of these products are buffered, the buffer or buffers used will help to maintain for a longer period the low acidic pH of the denture adhesive in the oral cavity, thus prolonging the oral environment having an acidic pH. An acidic environment will cause damage to the remaining natural teeth because the acid can decalcify hydroxyapatite in tooth enamel. Thus, adhesives that are inherently acidic can increase caries incidence and even predispose denture wearer to caries. The phenomenum is of particular concern to elderly denture wearers who are prone to xerostomia and root caries. Those wearing overdenture prostheses which are being supported by natural teeth as abutments are also at risk of having decalcification in the supporting natural teeth.

Another major drawback of almost all of the commercially available denture adhesives is that the adhesives do not easily dissolve in water, thus, making them difficult to wash off with water. Thus, remnants of an adhesive lodged in the recesses of a denture are very difficult, if not impossible, to be cleaned by simple washing with water.

For the foregoing reasons, it is clear that there is a need for a denture adhesive that meet all of the criteria discussed above.

SUMMARY

A method of adhering a denture, having a biocontact surface, to a gum or a roof of a mouth, containing the steps of (1) Treating the biocontact surface of the denture with a denture adhesive composition comprising a chemical substance derived from an aloe leaf to obtain a treated denture; and (2) placing the treated denture in close proximity to a gum or the roof of the mouth thereby engaging the treated denture with the gum or the roof of the mouth. A method of preparing a denture adhesive composition comprising a chemical substance derived from an aloe leaf by blending the required ingredients with water to obtain a substantially homogeneous composition.

DETAILED DESCRIPTION

Figure 1:
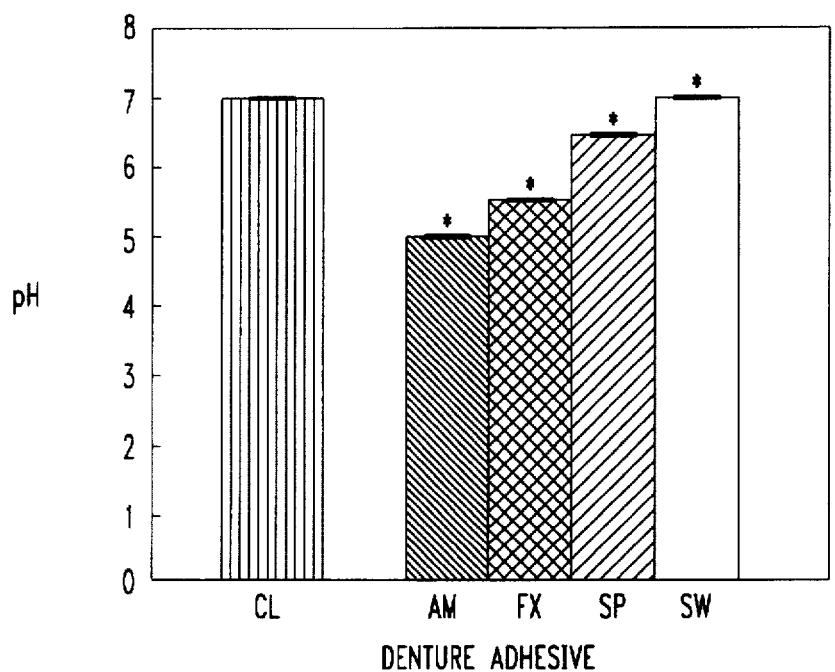
FIGS. 1–6 show the mean pH values over 24 hours for each concentration of a solution of various denture adhesives. The concentration of the solution is 5%, 3.3%, 2.5%, 2%, 1.3%, and 1% for FIGS. 1, 2, 3, 4, 5, and 6, respectively.

The problems discussed above, inherent in the currently commercially available denture adhesives have been solved in the embodiments of the present invention pertains, in one aspect, to the preparation and use of a denture adhesive containing substances isolated and derived from an aloe vera leaf. The substances can be concentrated gel from aloe, such as aloe vera gel extract, raw aloe gel, bulk acetylated mannan or bulk pharmaceutical mannan, and acemannan, all of which can be prepared, derived and isolated from aloe gel fillet.

Neither one of the aloe vera gel extract, bulk acetylated mannan from aloe and bulk pharmaceutical mannan from aloe is known either to be toxic or to cause an allergic reaction in a human at the level utilized. Rather, these substances have been reported to cause anti-inflammatory effects and to promote wound healing when used topically. They produce soothing effects to the tissues to which they have been applied. These substances from aloe do not contain formaldehyde. Further, these substances do not contain any detrimental amount of sodium salts. Moreover, these substances can be easily and completely washed off with water. If manufactured properly, these substances from aloe are essentially tasteless and they harbor no microorganisms.

As used herein, the term "active" means "bioactive." Bioactive denotes possessing biological activity, such as a pharmacological or a therapeutic activity.

Aloe gel fillet that is substantially anthraquinone-free can be produced by the following steps from a leaf of an aloe plant:

1. Washing the aloe leaf in a bactericidal solution to remove substantially all surface dirt and bacteria;
2. removing at least a first end portion from the washed leaf;
3. draining, preserving and collecting anthraquinone rich sap from the cut and washed leaf; and
4. removing rind from the leaf to produce a substantially anthraquinone-free gel fillet.

Aloe vera gel extract, known as "aloe raw gel," "raw gel," or "aloe juice," that is substantially anthraquinone-free having solubilized and suspended matter can be obtained by grinding and homogenizing the substantially anthraquinone-free aloe gel fillet.

Aloe vera gel extract containing active chemical substance(s) can be produced by the following steps:

1. Obtaining aloe raw gel, "raw get," or "aloe juice" having solubilized and suspended matter;
2. adding a water soluble, lower aliphatic polar solvent, such as ethanol, to the aloe juice to precipitate active chemical substance(s) and thereby forming a heterogeneous solution/suspension; and
3. removing the water soluble, lower aliphatic polar solvent and the solubilized matter from the heterogeneous solution to isolate the precipitated active chemical substance(s).

If desired, dried aloe vera gel extract (sometimes referred to as Aloe Vera Mucilaginous Polysaccharide ("AVMP®") powder) can be produced by drying, preferably freeze-drying, the precipitated active chemical substance(s) obtained above.

Another form of aloe vera gel extract containing active chemical substance(s) can be produced by the following steps:

1. Obtaining aloe raw gel, "raw gel," or "aloe juice" having solubilized and suspended matter;
2. adjusting the pH of the aloe juice to from about 3 to about 3.5;
3. adding a water soluble, lower aliphatic polar solvent, such as ethanol, to the aloe juice to precipitate active chemical substance(s) and thereby forming a heterogeneous solution/suspension; and
4. removing the water soluble, lower aliphatic polar solvent and the solubilized matter from the heterogeneous solution to isolate the precipitated active chemical substance(s).

If desired, dried aloe vera gel extract can be produced by drying, preferably freeze-drying, the precipitated active chemical substance(s) obtained above.

Generally, "bulk acetylated mannan" ("BAM"), or "bulk pharmaceutical mannan" ("BPM"), may be prepared from aloe leaves as follows:

1. Aloe leaves are washed, sliced open and filleted to remove the leaf rind. The clean (substantially anthraquinones free) inner gel is retained while the green rind is discarded.
2. The filleted material is homogenized (creparo) and extensively filtered with a Finisher Model 75 (FMC, Chicago, Ill.), to remove most of the pulp.
3. The clear viscous gel is acidified to a pH of approximately 3.2 with dilute HCl.
4. The acidified gel is then extracted with four volumes of 95% ethanol at ambient temperature. Floating material is removed, then the alcohol/water mixture is siphoned off while the solid precipitate is collected by centrifugation. Most alcohol/water soluble substances such as organic acids, oligosaccharides, monosaccharides, anthraquinones and inorganic salts are eliminated by the alcohol extraction process.
5. The solid aloe vera extract is then washed with fresh alcohol, centrifuged, freeze dried, and ground to a white powder. The product at this stage still contains some moisture, protein, monosaccharides, oligosaccharides, organic/inorganic salts and other substances. The product can be stored as a source of BPM. The product is stable at room temperature in the freeze-dried form for several years if protected from additional moisture. The detailed procedures for producing substantially anthraquinone-free aloe gel, for producing substantially anthraquinone-free aloe juice, for extracting active chemical substance(s) from an aloe leave, for preparing BPM and for extracting from an aloe leave substantially non-degradable lyophilized ordered linear polymer of mannoses have been described in U.S. Pat. Nos. 4,735,935, 4,851,224, 4,917,890, 4,957,907, 4,959,214, and 4,966,892, the entire content of each of which is incorporated by reference.

The uses of aloe products have been described in Carrington's U.S. Pat. Nos. 5,106,616, 5,118,673, 5,308,838, 5,409,703, 5,441,943, and 5,443,830, the entire content of each of which is hereby incorporated by reference.

Filtered and irradiated bulk pharmaceutical mannan ("FBA") can be prepared and produced by filtering the BPM (using a filter having a pore size of about 25 µm) followed by gamma irradiation (about 2.5 Mrad).

Various modifications of the disclosed processes to produce and to use denture adhesives containing chemical substances isolated and produced from an aloe vera leaf, as well as alternative modifications, variations and equivalents will become apparent to persons skilled in the art upon reading the above general description. The following examples are illustrative only and are not intended to limit the scope of the appended claims, which cover any such modifications, equivalents or variations.

EXAMPLE 1

PREPARATION OF BULK ACETYLATED MANNAN ("BAM") OR BULK PHARMACEUTICAL MANNAN ("BPM")

Aloe leaves suitable for use were washed in 0.02% calcium hypochlorite. After rinsing with water, leaf tips and butts were removed, and leaves were inspected once again for damaged areas which were trimmed away.

Cleaned, trimmed leaves were filleted by hand or are fed by hand into the slitter, which separated the outer leaf rind from the leaf pulp. Fillets were funneled into a grinder; rinds were collected for disposal. The ground aloe gel discharged from the grinder was collected in covered stainless steel tanks.

The tank containing the ground aloe gel was moved to an area where the gel was homogenized in a Crepaco homogenizer. The homogenized gel or "raw gel" was discharged into another stainless steel tank and transferred to the finisher area for filtration.

The raw gel was then pumped through the finisher, a horizontal screw-type extractor (FMC), to filter out the pulp which was discarded. One hundred gallons of filtered gel was pumped into a 100-gallon stainless steel tank.

The filtered gel was then adjusted with 6N hydrochloric acid to a pH of approximately 3.2.

The pH adjusted gel was "ethanol precipitated" by adding the gel to the alcohol at ambient temperature at a ratio of 1 part gel to 4 parts alcohol and mixed in a 550 gallon stainless steel tank until the flocculent precipitate formed.

Once the precipitate formed, the batch was mixed slowly while being transferred by a positive displacement pump to a continuous flow Sharples centrifuge for collection of the BAM or BPM which was then freeze-dried under reduced pressure of about 100 mTorr. Shelf temperature was set at −30° C.; the product was freeze-dried for approximately 24 hours or until all temperature probes reached −30° C.

EXAMPLE 2

DENTURE ADHESIVE CONTAINING ALOE EXTRACT

Broadly, the denture adhesive of the present invention is made from concentrated gel from aloe. Optionally, a dispersant or a thickener, or both, can be incorporated into the denture adhesive of the present invention.

The concentrated gel from aloe can be aloe raw gel, aloe vera gel extract, bulk acetylated mannan ("BAM") or bulk pharmaceutical mannan ("BPM"), extracted carbohydrate from aloe gel, carbohydrate isolated derived from aloe, freeze-dried aloe gel, acemannan, Carrasyn®, and other fractions derived from aloe gel. The fractions can be derived by centrifugation, filtration, ultrafiltration, chromatography, dialysis, selective precipitation, pH adjustment, irradiation, homogenizing or a combination of such processes.

The weight percent, based on the total weight of the denture adhesive composition, of the concentrated gel from aloe used during the preparation of the denture adhesive of the present invention can range from about 0.005% to about 1%; preferably in the range of from about 0.1% to about 0.6%; and most preferably in the range from about 0.1% to about 0.3%.

A dispersant (or a protective colloid, a suspending agent, a stabilizer, or an emulsifier) can be selected from a wide variety of materials. Non-limiting examples include glycerine, a polyvinylpyrrolidone ("PVP"), or a PVP K homopolymer, such as: PVP K-15 powder having an average molecular weight ("Mv") of 8000 Daltons; PVP K-30 powder, Mv 38,000 Daltons; PVP K-60, 45% solution, Mv 216,000 Daltons; PVP K-90 powder, Mv 630,000 Daltons; or PVP K-120 powder, Mv 2,900,000 Daltons. Other dispersants include a series of vinylpyrrolidone ("VP")/vinyl acetate ("VA") copolymers, which copolymers covering a range of VP/VA mole ratios [given in bracket], supplied as either ethanol solution ("E"), isopropanol solution ("I"), or solid ("S"), PVP/VA E-735 [70/30], PVP/VA E-635 [60/40], PVP/VA E-535 [50/50], PVP/VA E-335 [30/70], the corresponding isopropanol solution and PVP/VA I-235 [20/80], PVP/VA S-630 [60/40]. Other dispersants include: Polyvinylpyrrolidone, pharmaceutical grade, known as Povidone USP or Polyvidonum, some of which are supplied as Plasdone C-15, Plasdone C-30, Plasdone K-25, Plasdone K-25, Plasdone K-26/28, Plasdone K-29/32, Plasdone K-90, or Plasdone K-120. Another class of dispersant is Crospovidone NF Polyvidonum insoluble, crosslinked N-vinyl-2-pyrrolidone. Still other dispersant includes: Poly(methyl vinyl ether/maleic anhydride) (linear interpolymer with 1:1 molar ratio) Series of copolymers, supplied as Gantrez® AN-119, having molecular weight as determined by membrane osmometry ("M.Wt.") of 20,000, Gantrez® AN-139 M.Wt. 41,000, Gantrez® AN-149 M.Wt. 50,000, and Gantrez® AN-169 M.Wt. 67,000.

The dispersant is sometimes termed a protective colloid, a suspending agent, or an emulsifier.

The weight percent, based on the total weight of the denture adhesive composition, of the dispersant used in the manufacture of the denture adhesive of the present invention can range from about 1% to about 15%; preferably in the range of from about 5% to about 10%; and most preferably in the range from about 5% to about 7%.

Exemplary thickeners useful in this invention include: Those which are organic in nature (such as karaya gum, acacia gum, tragacanth, gelatin, pectin, methylcellulose, hydroxymethylcellulose, and sodium carboxymethylcellulose) or synthetic polymers (such as polyethylene oxide, vinyl methyl ether/maleic anhydride compounds, cationic polyacrylamide compounds, or acetic polyvinyl). Many of these are largely carbohydrates or carbohydrate-like and swell with the addition of water. Preferably the thickeners are hydroxyethylcelluloses, such as Natrosol H (38000 cp), Natrosol 250 G Pharm (150–200 cp), and Natrosol 250 GL (75–150 cp).

The weight percent, based on the total weight of the denture adhesive composition, of the thickener used in the preparation of the denture adhesive of the present invention can range from about 2% to about 15%; preferably in the range of from about 5% to about 12%; and most preferably in the range from about 7% to about 10%.

In addition to the foregoing materials, the denture adhesive composition may be formulated or manufactured with additional optional components well known in the denture adhesive art. Such optional materials utilized in the invention may include hydrogen peroxide, preservatives, flavoring agents, colorants, sweetening agents and so forth.

Optionally, dilute hydrogen peroxide can be added to the "pre-mixture" during the preparation and manufacture of the denture adhesive of the present invention. The weight percent, based on the total weight of the denture adhesive composition, of the dilute hydrogen peroxide (about 3%) used during the manufacturing process can range from about 5% to about 25%; preferably in the range of from about 10% to about 20%; and most preferably in the range from about 15% to about 20%.

Another optional ingredient is a preservative. Preservatives which may be useful in the manufacture of the denture adhesive formulations of the present invention include those known antimicrobial agents conventionally employed in the art, such as sodium borate and sodium tetraborate; hexachlorophene; benzoic acid, propylhydroxy benzoate, and sodium benzoate; the parabens; sorbic acid and sorbates; propionic acid and propionates; acetic acid and acetates; nitrates and nitrites; sulfur dioxide and sulfites; antibiotics; diethyl pyrocarbonate; epoxides and phosphates. The parabens include the methyl, ethyl, propyl and butyl esters of parahydroxybenzoic acid. Preferred preservative includes benzethonium chloride and methyl paraben. The weight percent, based on the total weight of the denture adhesive composition, of the preservative used in the preparation of the denture adhesive of the present invention can range from about 0.002% to about 0.5%; preferably in the range of from about 0.02% to about 0.3%; and most preferably in the range from about 0.1% to about 0.15%.

Yet another optional ingredient is a buffering agent. Common buffering agents include salts of phosphate, sodium hydroxide, potassium hydroxide, citric acid, acetic acid, and hydrochloric acid. The weight percent, based on the total weight of the denture adhesive composition, of the buffer used in the preparation of the denture adhesive of the present invention can range from about 0.05% to about 15%; preferably in the range of from about 3% to about 10%; and most preferably in the range from about 3% to about 7%.

Still another optional ingredient is a chelating agent. A common chelating agent is disodium EDTA. The weight percent, based on the total weight of the denture adhesive composition, of the chelating agent used in the preparation of the denture adhesive of the present invention can range from about 0.05% to about 0.4%; preferably in the range of from about 0.1% to about 0.3%; and most preferably in the range from about 0.1% to about 0.2%.

Another optional ingredient is a filler, such as magnesium oxide, wetting agent (sodium lauryl sulfate) and plasticizing agent. In general when a filler is used, it can range from about 1% to about 25% of weight, based on the total weight of the denture adhesive.

Yet another optional ingredient is a flavoring agent. Flavoring agents, preferably water soluble, well known to the denture adhesive art may be added during the manufacture of the instant invention. These flavoring agents may be chosen from synthetic flavor oils and/or oils derived from plants, leaves, flowers, fruits and so forth and combinations thereof. Representative flavoring agent includes: spearmint oil, cinnamon oil, oil of wintergreen (methylsalicylate), vanilla, and peppermint oils. Also useful are artificial, natural or synthetic fruit flavors such as citrus oil including lemon, orange, grape, lime and grapefruit, and fruit essences including apple, strawberry, cherry, pineapple and so forth. The flavoring agent may be a liquid, sprayed dried, encapsulated, absorbed on a carrier and mixtures thereof The weight percent, based on the total weight of the denture adhesive composition, of the flavoring agent used in the preparation of the denture adhesive of the present invention can range from about 0.01% to about 5%; preferably in the range of from about 0.05% to about 1%; and most preferably in the range from about 0.1% to about 0.2%.

Yet another optional agent that can be used during the manufacture of the denture adhesive of the present invention is a sweetening agent. The sweetening agent may be selected from a wide range of materials, including water-soluble agents, water-soluble artificial sweeteners, and dipeptide based sweeteners, and mixtures thereof Usable sweetening agents include: xylose, ribose, glucose, mannose, galactose, fructose, dextrose, sucrose, sugar, maltose, corn syrup, sorbitol xylitol, mannitol, maltitol, saccharin salts, cyclamate salts, sucralose, L-aspartyl-L-phenylalanine methyl ester and the like.

In general, the amount of sweetener will vary with the desired amount of sweetener selected for a particular denture adhesive formulation. The weight percent, based on the total weight of the denture adhesive composition, of the sweetening agent used in the preparation of the denture adhesive of the present invention can range from about 0.01% to about 1%; preferably in the range of from about 0.05% to about 0.5%; and most preferably in the range from about 0.1% to about 0.2%.

Still another optional ingredient is a colorants. Colorants useful in the present invention include pigments such as titanium dioxide, dyes suitable for food, drug and cosmetic applications. These colorants are known as F.D. & C dyes. F.D.& C. Colorants and their corresponding chemical structures may be found in the Kirk-Othmer Encyclopedia of Chemical Technology, 3rd Edition, in Vol. 6. In general, colors when used are employed in the amount of about 0.005% to about 0.5% by weight of the denture adhesive compositions.

A. One embodiment of the denture adhesive of the present invention was made by mixing and blending the following ingredients:

|  | Weight % |
|---|---|
| Bulk Acetylated Mannan ("BAM") | 0.1 |
| PVP K-30 | 5.7 |
| Natrosol 250 G | 5.1 |
| Hydrogen Peroxide (3%) | 17.2 |
| Water | 71.9 |

The weight percent given was based on the total weight of the denture adhesive composition.

B. Another embodiment of the denture adhesive of the present invention was made by mixing and blending the following ingredients:

|  | Weight % |
|---|---|
| BAM | 0.1 |
| PVP K-29/32 | 5.7 |
| Natrosol 250 G | 5.1 |
| Hydrogen Peroxide (3%) | 17.2 |
| Benzethonium Chloride | 0.050 |
| Water | 71.9 |

The weight percent given was based on the total weight of the denture adhesive composition.

C. Still another embodiment of the denture adhesive of the present invention was made by mixing and blending the following ingredients:

|  | Weight % |
|---|---|
| BAM | 0.1 |
| PVP K-29/32 | 5.7 |
| Natrosol 250 H | 4.0 |
| Hydrogen Peroxide (3%) | 17.2 |
| Benzethonium Chloride | 0.025 |
| Water | 73.0 |

The weight percent given was based on the total weight of the denture adhesive composition.

D. Yet another embodiment of the denture adhesive of the present invention was made by mixing and blending the following ingredients:

|  | Weight % |
|---|---|
| BAM | 0.2 |
| PVP K-29/32 | 5.7 |
| Natrosol 250 H | 2.0 |
| Hydrogen Peroxide (3%) | 17.2 |
| Benzethonium Chloride | 0.025 |
| Water | 74.9 |

The weight percent given was based on the total weight of the denture adhesive composition.

E. Another embodiment of the denture adhesive of the present invention was made by mixing and blending the following ingredients:

|  | Weight % |
|---|---|
| BAM | 0.2 |
| PVP K-29/32 | 5.7 |
| Natrosol 250 H | 3.0 |
| Hydrogen Peroxide (3%) | 17.2 |
| Benzethonium Chloride | 0.050 |
| Water | 73.8 |

The weight percent given was based on the total weight of the denture adhesive composition.

F. Another embodiment of the denture adhesive of the present invention was made by mixing and blending the following ingredients:

|  | Weight % |
|---|---|
| Acemannan | 0.100 |
| Povidone | 1.000 |
| Natrosol 250 H | 0.900 |
| Hydrogen Peroxide (3%) | 0.260 |
| Benzethonium Chloride | 0.004 |
| Water | 97.736 |

The weight percent given was based on the total weight of the denture adhesive composition.

G. Yet another embodiment of the denture adhesive of the present invention was made by mixing and blending the following ingredients:

|  | Weight % |
|---|---|
| BAM | 0.2 |
| PVP K-29/32 | 5.7 |

-continued

| | Weight % |
|---|---|
| Natrosol 99-250 G. Pharm | 10 |
| Methyl Paraben | 0.1 |
| Benzethonium Chloride | 0.05 |
| Di Sodium EDTA | 0.1 |
| Sodium Hydroxide 0.1N | 5 |
| Nutrasweet | 0.2 |
| Water | 78.66 |

The weight percent given was based on the total weight of the denture adhesive composition.

EXAMPLE 3

PREPARATION OF DENTURE ADHESIVE CONTAINING ALOE EXTRACT

One embodiment of the denture adhesive of the present invention was prepared by the following steps:

1. Mixing the required amounts of concentrated gel from aloe, dispersant, thickener, and any other optional ingredients to give a mixture;
2. Adding water to the mixture of ingredients to give a mixture containing water; and
3. Blending the mixture containing water to give a relatively homogenous final mixture.

Alternatively, a mixture of relatively dried ingredients was added to the water followed by mixing and blending to give a relatively homogeneous final mixture. If desired, the relatively homogenous mixture can then be dried, preferably by freeze drying, to give a solid or a sheet of foam. The solid can then be ground to powder.

Alternatively, another embodiment of the denture adhesive of the present invention was prepared by:

1. Heating water to a temperature between about 35° and 60°;
2. Adding preservative to the heated water with stirring so as to dissolve the preservative in the water; and
3. Mixing and blending other ingredients into the water having the preservative dissolved therein to give a relatively homogeneous final mixture.

If desired, the relatively homogeneous final mixture can then be dried, preferably by freeze drying, to give a solid or a sheet of film. The solid can then be ground to powder.

The denture adhesive of the present invention can be prepared in the form of a solid powder, foam, paste, film or gel by known methods.

EXAMPLE 4

USE OF DENTURE ADHESIVE CONTAINING ALOE EXTRACT

Ordinarily, the dentures must first be thoroughly cleaned. A small amount of the denture adhesive of the present invention is then applied evenly to all surfaces of the denture coming into contact with the gums or the roof of the mouth, namely, the biocontact surfaces. Excess denture adhesive is then removed. If the adhesive used is in the form of a solid powder or foam, a small amount of water or other fluid can be added to the denture adhesive to create a "wet" denture adhesive. Alternatively, the denture can be left wet before applying the solid powder or foam of the denture adhesives. Then the "wet" denture adhesive is spread with a finger or other applicator to create a thin and even layer over the entire contact area of the denture. If the adhesive used is in the form of a paste or thick gel, no "pre-wetting" or "post-wetting" is usually necessary. Again, it is preferably to spread the adhesive to create a thin and even layer of the adhesive over the entire contact area of the denture.

The denture having a thin layer of denture adhesive is then placed on the location and secured in place under pressure.

Depending on the desired length of holding the denture to the mouth, a patient would usually start out using as little of the adhesive as possible. The amount of the adhesive can be increased until the denture is held securely in the mouth for the desired duration.

EXAMPLE 5

EVALUATION OF DENTURE ADHESIVE CONTAINING ALOE EXTRACT

Materials and Methods

Determination of pH

Denture adhesives tested in this study were: (a) Super Wernet's powder ("SW") from Block Drug Company; (b) Super Poli Grip cream ("SP") from Block Drug Company; (c) Fixodent Fresh ("FX") from Proctor and Gamble; and (d) denture adhesive of this invention containing "Acemannan Freeze-Dried Wafer" ("AM"). For the sake of simplicity, one embodiment of the present invention of denture adhesive containing Acemannan Freeze-Dried Wafer is sometimes referred to as "Acemannan Wafer." "Acemamlian Wafer" is composed mainly of water, hydroxyethylcellulose, hydrogel of aloe vera gel extract, and benzethonium chloride. Super Weinet's powder was composed mainly of hydroxypolyenes (oxyethylenes) and sodium carboxymethylcellulose. Super Poly Grip had a hydrocarbon oil and a hydrocarbon wax, hydroxypolyenes, and sodium carboxymethylcellulose. Fixodent Fresh contained a hydrocarbon oil, a copolymer with maleic anhydride, and a polysaccharide derivative, called sodium alginate. R Koppang, et al., "A Method for Testing Denture Adhesive," *J. Prosth. Dent.*, 73:486–491 (1995), the entire content of which is hereby incorporated by reference.

Samples of each material were weighed and mixed with deionized water (1 g/20 ml to make a 5% solution) until a uniform gel was formed. Serial dilutions were then performed to establish solutions of 3.3%, 2.5%, 2%, 1.3%, and 1%. A separate sample of pure deionized water served as the control. Immediately following preparation of the samples, pH values were determined for each dilution and the deionized water control. The pH was measured using a glass pH electrode with a salt bridge and a Beckman pHI-50 pH meter. Following the initial pH readings, all the samples as well as the control were measured at 1, 2, 3, 4, 5, 6, 12, and 24 hour intervals. All sample dilutions and the control were stored at 25° C. during the testing procedures.

Cytotoxicity Test

Cytotoxicity of each sample was assessed using the in vitro tetrazolium-based MTT calorimetric assay. The dye utilized for this assay was a tetrazolium salt, 3-(4,5-dimethylthiazol-2-yl)2,5 diphenyltetrazolium bromide (MTT), hence the name MTT assay. This method is a widely accepted, reliable, and sensitive test for measuring cell viability as well as for quantitatively assessing the compatibility between cells and biomaterials. It has the advantages of reproducibility, simplicity, cost effectiveness, and lack of radioactive waste. G. Ciapetti, "In Vitro Evaluation of Cell/Biomaterial Interaction By MTT Assay," *Biomaterials*, 14:359–364 (1993), the entire content of which is hereby incorporated by reference. The MTT assay measured the mitochondrial succinic dehydrogenase activity in cells.

Basically, the test is based on the fact that since mitochondrial function is related to adenosine triphosphate ("ATP") production and is steady and at maximal conditions in vital cells, it can be utilized to estimate the number of viable cells in a particular culture. T. Mosmann, "Rapid Calorimetric Assay for Cellular Growth and Survival: Application To Proliferation and Cytotoxic Assays," *J. Immunol. Methods*, 65:55–63 (1983), the entire content of which is hereby incorporated by reference. Mitochondria synthesize ATP from carbohydrates, proteins, and lipids between their inner and outer membrane via the Krebs cycle. Succinate is reduced to fumarate by succinic dehydrogenase ("SDH") early in the Krebs cycle. To complete this reduction, FAD is needed to carry hydrogen via $FADH_2$. In the in vitro reaction, the $FADH_2$ reduces the tetrazolium salt (MTT) to formazan. Formazan is blue and precipitates in the mitochondria because it is insoluble. Disodium succinate is a required substrate for this assay. When the reaction is complete, a color change from yellow to blue takes place and degree of completion is directly proportional to the enzymatic reaction of the tetrazolium salt. The crystalline MTT-formazan product is dissolved by dimethyl sulfoxide prior to spectrophotometry. A spectrophotometer is used to read the optical density of the blue color in liquid aliquots at 550 nm. The optical density is reasonably comparable to the mitochondrial activity and the number of viable cells. F. Denziot, et al., "Rapid Calorimetric Assay for Cell Growth and Survival. Modification to the Tetrazolium Dye Procedure Giving Improved Sensitivity and Reliability," *J. Immunol. Methods*, 89:271–277 (1986). The optical densities are then used to compare the toxicity of various substances placed in the culture media to the control in which no substances are added to the culture media. Dose-response curves can be plotted at a given time to delineate the toxic concentration that kills 50% of the cells ($TC_{50}$). Additionally, different substances can be compared based on toxicity expressed as a percentage of blue reaction product relative to the control (maximum blue intensity).

The population of cells utilized for the purposes of determining the cytotoxicity of the denture adhesives represented human gingival fibroblasts (HGF) only recently commercially available from ATCC. HGF were cultured in petri dishes in 10 ml RPMI-1640-L-glutamine supplemented with 100 units/ml penicillin, 100 mg/ml streptomycin, and 10% fetal bovine serum. The cultures were maintained at 37° C., 5% $CO_2$, with 95% air and saturated humidity. After incubating stock cultures for two weeks in petri dishes, media was removed and each dish was washed with filtered, phosphate buffered saline to remove excess media. Trypsin (10% in PBS) was then applied to remove the attachment of the fibroblasts to the bottom of the dishes. Cell detachment was verified with light microscopy. Cell suspensions were harvested and spun down in a centrifuge (3000×G). A Neubaurer hemocytometer (0.01 mm deep) was used for counting the cells. A 20 ml cell suspension was added to each well of a 12-well microplate yielding 25,000 cells per well. Following a 24 hour incubation period, each denture adhesive was placed at a 1% concentration in fresh media into the wells of the microplates. These solutions were incubated for 3, 6, 12, and 24 hours respectively at 37° C. Following the elapsed time for each incubation period, the culture medium supernatant was then removed and wells were washed with PBS and 2 ml of MTT solution containing 30 mg MTT powder 3-(4,5-dimethylthiazol-2-yl)2,5 diphenyltetrazolium bromide, 15 ml of distilled water, 7.5 ml of 0.2M Tris Buffer, 3 ml of 0.005M magnesium chloride, 1.5 ml of 0.05M cobalt chloride, 3 ml of disodium succinate, and 12 µl of 10N hydrochloric acid was added to each well. The microplates were then allowed to incubate for 60 minutes. The MTT solution was removed and each well received 1 ml 10% neutral buffered formalin for 10 minutes to fix the cells. At this point, it was possible to identify formazan in the nuclei of HGF using a Confocal microscope. Formaldehyde was then removed and the cells were washed with sterile distilled water and allowed to dry. A 1 ml solution of dimethyl sulfoxide and 50 µl NAOH was then added to each well to dissolve the blue formazan product. The microplates were shaken for ten minutes prior to removal of the liquid from each well and placement into labeled cuvettes. Optical densities were measured in a spectrophotometer at 550 nm.

Strength Test

Denture adhesives are subject to destruction, dilution, and dissolution over time when exposed to the oral environment. The methodology utilized in this study to measure bond strength simulates the in vivo behavior of denture adhesives. F. Floystrand, et al., "An Experimental Model For Testing Denture Adhesive," *J. Prosth. Dent.*, 66:501–504 (1991), the entire content of which is hereby incorporated by reference. The method measures denture adhesive bond strengths in vitro between acrylic resin samples producing reliable and valid data.

This data, although collected in an accelerated manner, corresponds with achieved values for in vivo testing of denture adhesive performance. F. Floystrand, et al., "An Experimental Model For Testing Denture Adhesives In Vivo," *J. Dent. Res.*, 64:768 (1985), the entire content of which is hereby incorporated by reference.

The denture adhesives in this study were subjected to tensile strength testing for comparative evaluation of performance over time. Four methylmethacrylate resin (Lucitone 199) cylinders were heat processed and milled to 5 cm in height and 3 cm in diameter. This material is a commonly used resin for the fabrication of complete dentures and served as one of the bonding surfaces for all denture adhesives. The resin cylinders were then prepared for the tensile testing apparatus by drilling ³⁄₃₂" sink holes to receive ¹³⁄₁₆" screw eyes. Two holes were placed opposite each other on the tops of the resin cylinders and 1¼" machine screws and #6–32 nuts were placed through the eyes. The testing apparatus utilized was the Instron Universal Testing Machine, model #1125. The cylinders were attached to this machine and a 9" chain was attached to the superior universal head of the machine with an S-hook at the end for connection to the resin cylinder. This arrangement allowed for a universal joint which eliminated unwanted torquing when the tensile force was applied.

The denture adhesives were then tested by applying 0.1 gm of the material to the dry, inferior surface of the resin cylinders. The resin samples were then gently pressed against the polished acrylic resin bottom surface of a dry 9.5 cm diameter vacuum mixing bowl. A 2 kg weight was applied to the top of the resin cylinders for 15 seconds to assure a consistent application force for all of the adhesives tested. Immediately following the 2 kg application force, each dry assembly was placed into the Instron machine for initial strength value measurement. Deionized water (37° C.) was placed in the bowl to cover ⅔ of the resin cylinders.

At this time, initial bond strengths were obtained with the Instron for the wet condition. The assemblies were then placed into the heated water bath of a thermocycling device in which the water was held at a constant temperature of 37° C. The specimens were allowed to remain in the water bath for 3, 6, 9, 15, and 20 minutes. After the appropriate times had elapsed, the assemblies were removed from the thermocycling device and attached to the Instron machine with the water remaining in the bowls and connected to the chain with the S-hook. The Instron machine was calibrated to five pounds prior to use and set at a cross head speed of 0.5"/minute to provide a snap type of tensile force. The chart paper speed was 2.0 cm/minute and the load cell was 1000 pounds, which was acceptable for tensile testing. The force that was required to pull the resin cylinders away from their respective bowl was then applied, measured, and recorded. Each denture adhesive was tested five times at each time interval. Between tests, the bowls were cleaned thoroughly and the resin cylinders were lightly abraded with 600 grit sand paper to prevent possible contamination. Following the tensile testing, photographic documentation was made of the specimens to subjectively characterize the bond failure modes. Statistical analyses were completed for all data collected utilizing an overall one-way analysis of variance (ANOVA) and Tukey-Kramer multiple comparison tests.

Results

Figure 2:
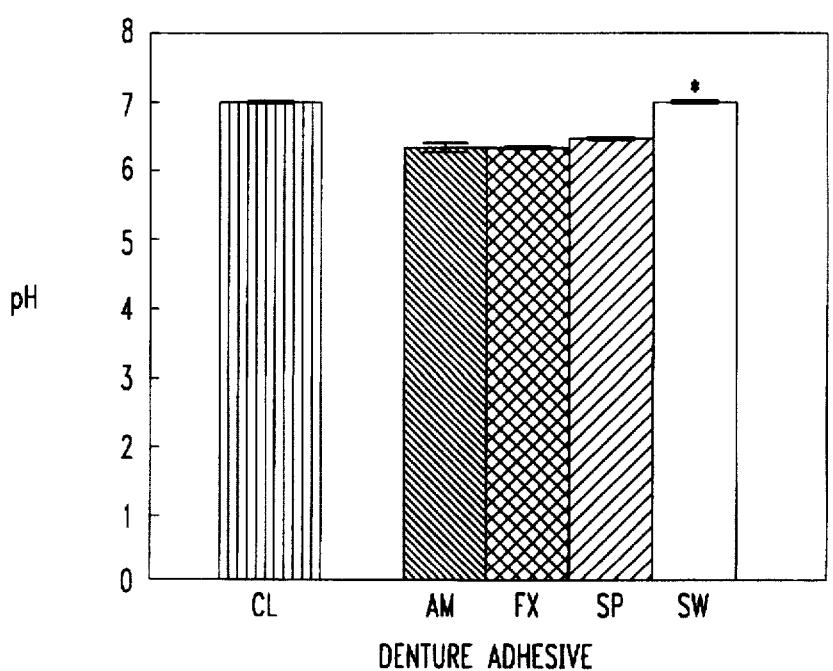
Figure 3:
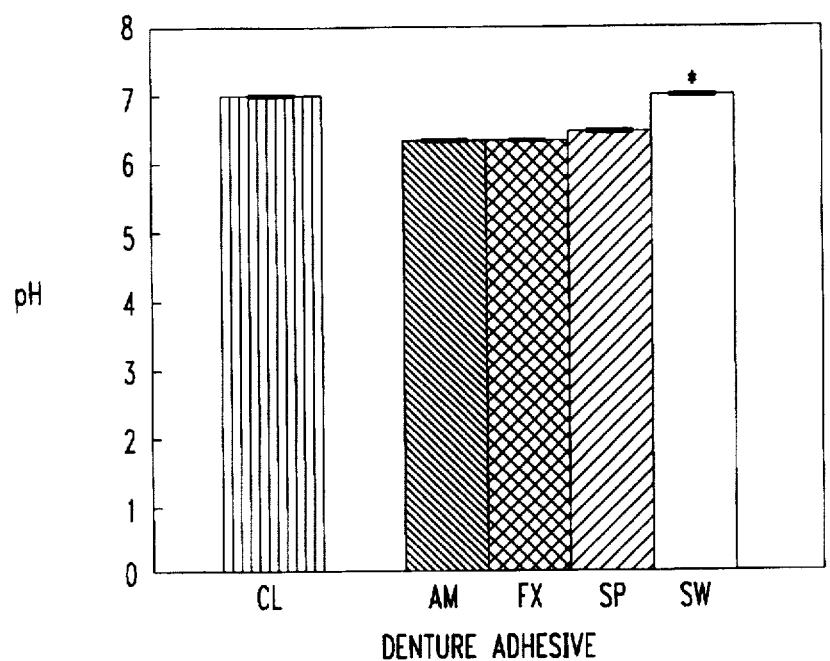
Figure 4:
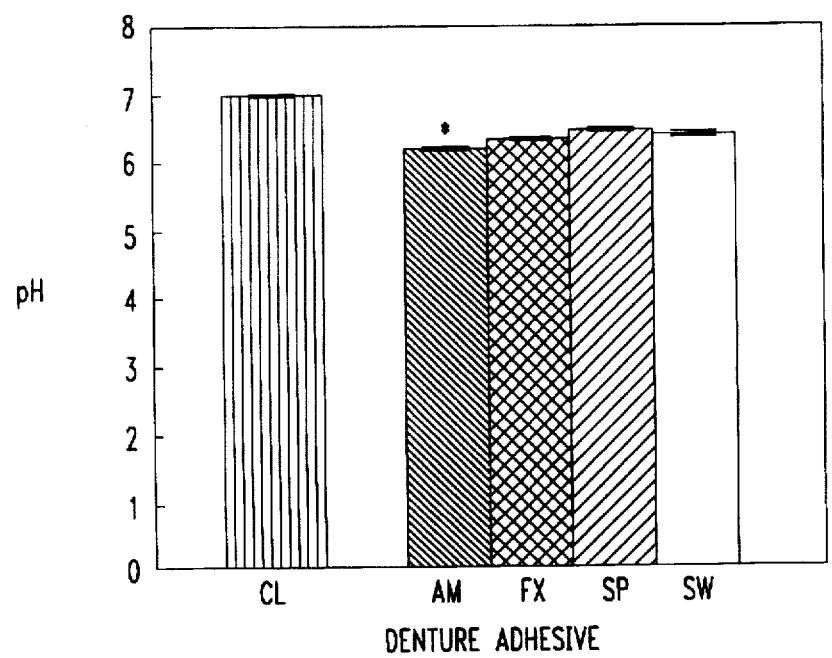
Figure 5:
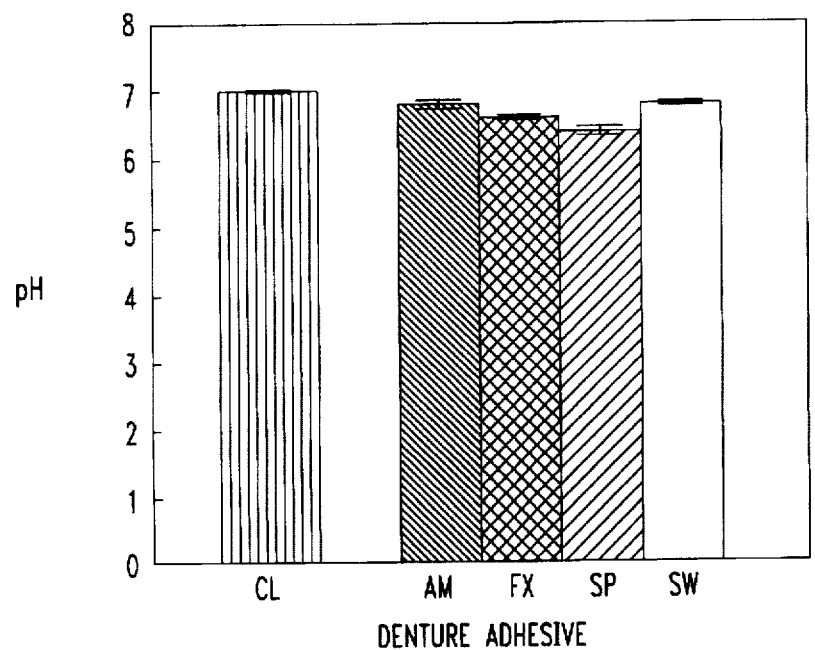
Figure 6:
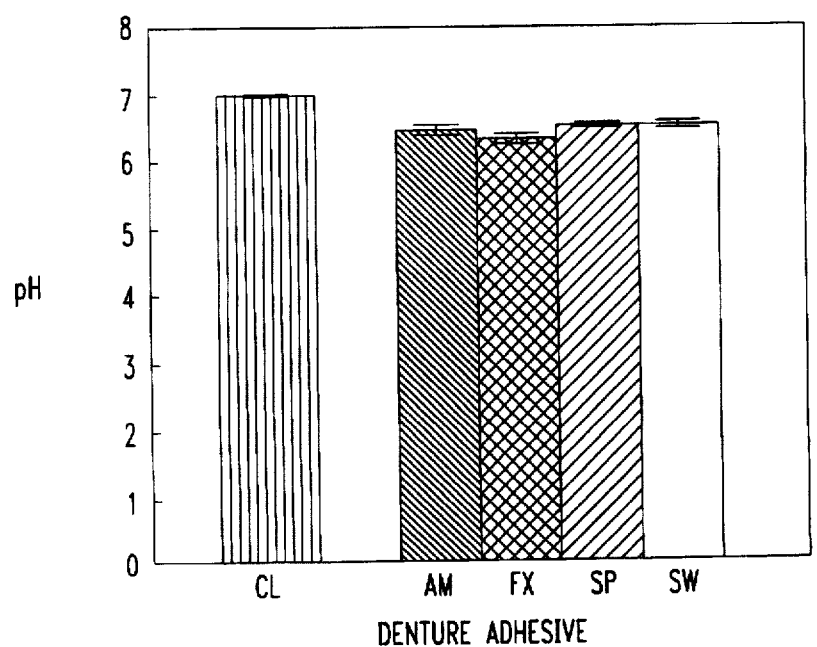

The pH tests indicated that within each dilution, minimal pH changes occurred in all of the materials over time. The mean pH values over 24 hours for each dilution of adhesive tested are illustrated in FIGS. 1–6. "CL" denotes control in the figures. Note the extremely small SEM values which indicate pH stability over time. Also, note that at 5% concentration, all mean pH values are significantly different (FIG. 1). Denture adhesive of the present invention, "Acemannan Wafer," was a significantly more acidic 5% solution than Super Wernet's, Fixodent Fresh, and Super Poli Grip ($P<0.001$). At 3.3% and 2.5% concentrations, Super Wernet's adhesive has a significantly greater mean pH compared to all other products (FIGS. 2 and 3, respectively). At 2% concentration, Acemannan Wafer has a significantly lower mean pH than all other adhesives (FIG. 4). At concentrations of 1.3% and 1%, there were no significant mean pH differences between adhesives (FIGS. 5 and 6, respectively).

Figure 7:
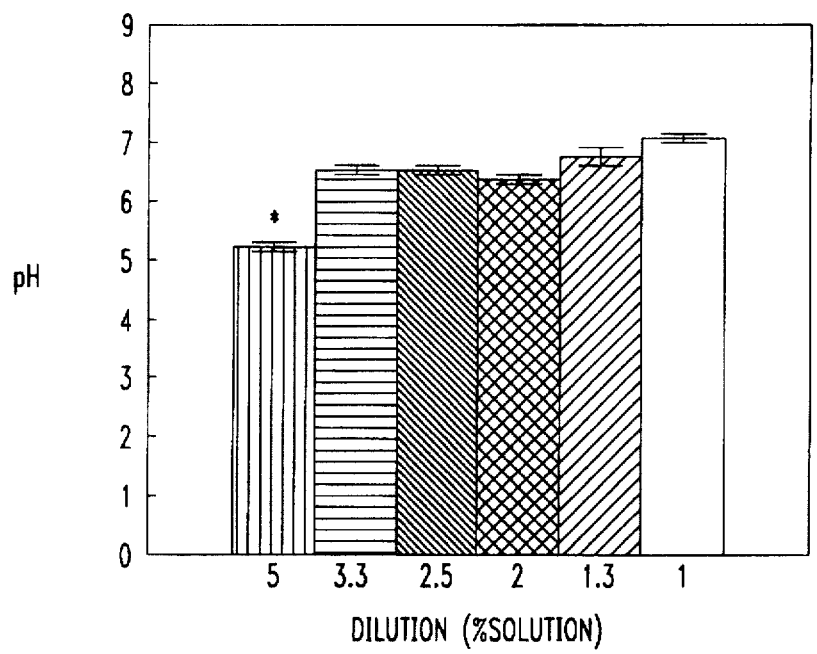
FIGS. 7–10 show changes in the mean pH values at different concentration of a solution of various denture adhesives. The denture adhesive is Acemannan Wafer ("AM"), Super Wernet ("SW"), Fixodent Fresh ("FX"), and Super Poli Grip ("SP") for FIGS. 7, 8, 9, and 10, respectively.
Figure 8:
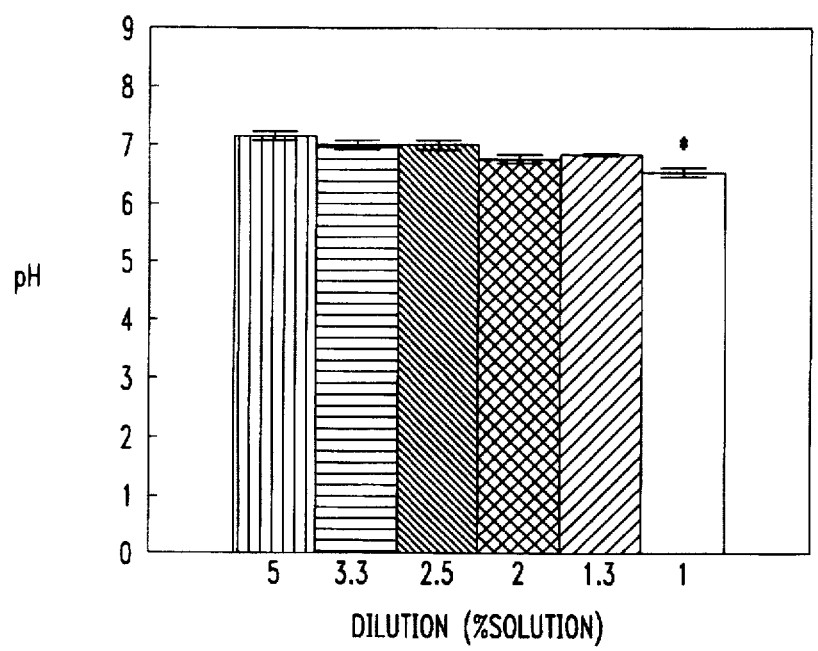
Figure 9:
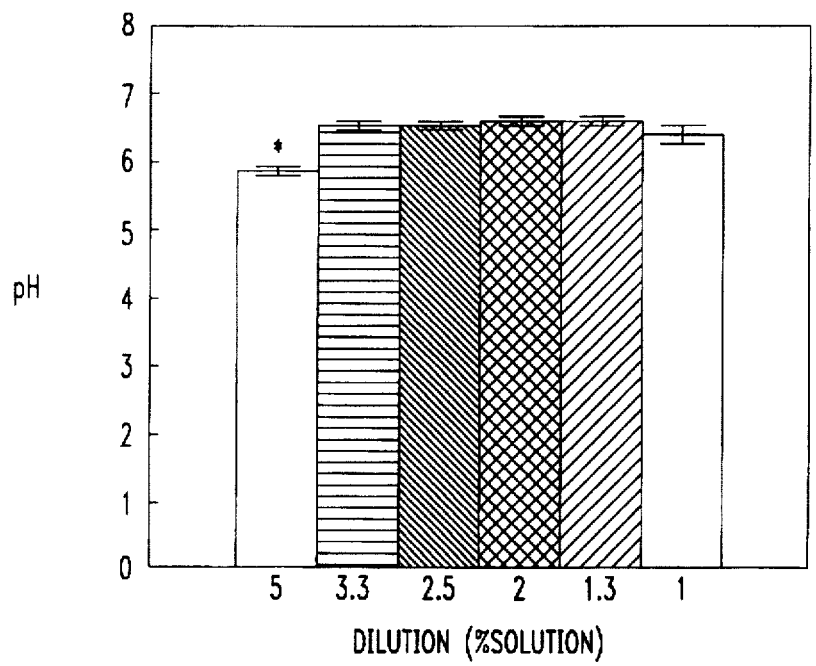
Figure 10:
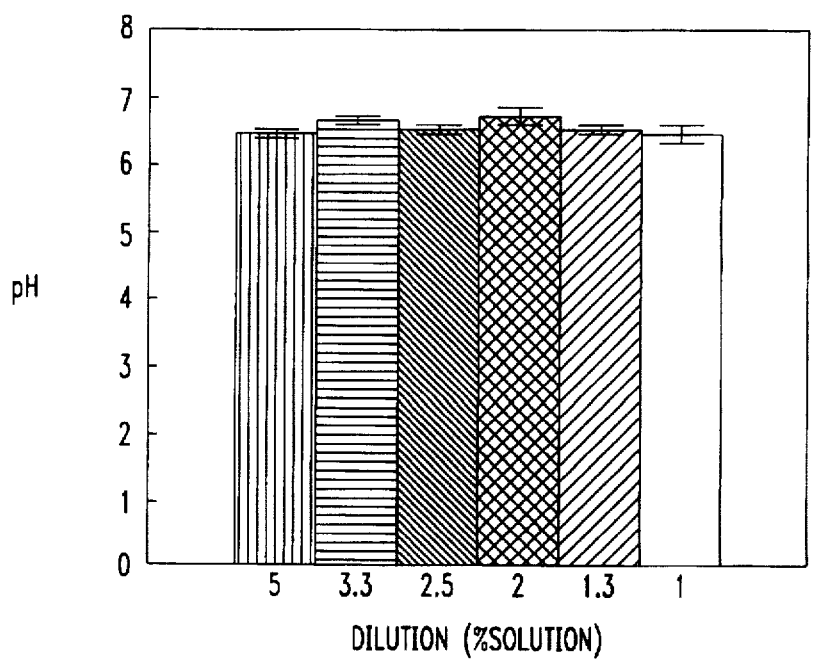

Some of the materials exhibited significant pH changes when they were diluted as illustrated in FIGS. 7–10. Mean pH of Acemannan Wafer at a 5% solution was significantly different than its respective 3.3%, 2.5%, 2%, 1.3%, and 1% solutions ($P<0.001$) with the mean pH values generally becoming more alkaline with increased dilution (5% mean pH of 5.2±0.2 vs. 1% mean pH of 6.3±0.1) (FIG. 7). The mean pH of the 1% Super Wernet's solution was significantly different than all other % solutions ($P<0.001$) with the mean pH generally becoming more acidic (5% mean pH of 7.2±0.2 vs. 1% mean pH of 6.4+0.1) (FIG. 8). Fixodent Fresh at a 5% solution had significantly different mean pH values than its 3.3%, 2.5%, 2%, 1.3%, and 1% solutions ($P<0.001$) with the values generally becoming more alkaline (5% mean pH of 5.8±0.1 vs. 1% mean pH of 6.2±0.2) (FIG. 9). Super Poli Grip exhibited minimal pH changes overall (5% mean pH of 6.5±0.2 vs. 1% mean pH of 6.4±0.1) (FIG. 10).

The pH values of each product at specific times for all dilutions were also evaluated. At all dilutions, Acemannan Wafer and Fixodent Fresh exhibited a progressive increase in pH over time. Super Wernet's demonstrated a progressive decrease in pH over time at all dilutions while Super Poli Grip remained relatively pH stable over time at all dilutions. Super Wernet's and Super Poli Grip remained above the critical pH value for dissolution of hydroxyapatite (pH=5.5) at all dilutions and timepoints while the pH values for Acemannan Wafer and Fixodent Fresh remained below the critical pH for each dilution and timepoint.

Figure 11:
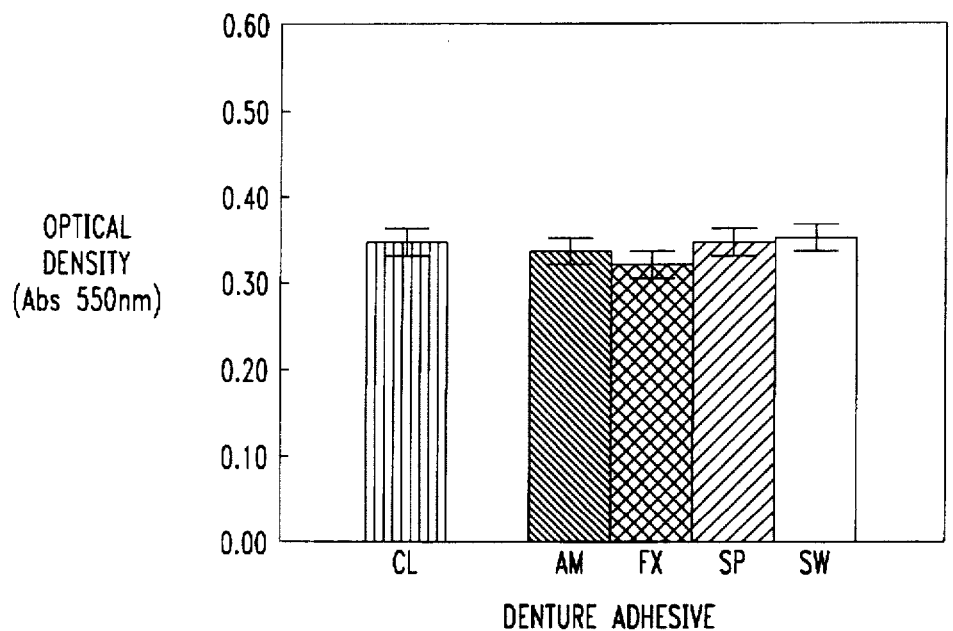
FIGS. 11–14 show MTT cytological assay of cell viability, given in optical density, expressed by different denture adhesives after various incubation times. The incubation time is 3 hours, 6 hours, 12 hours, and 24 hours for FIGS. 11, 12, 13, and 14, respectively.
Figure 12:
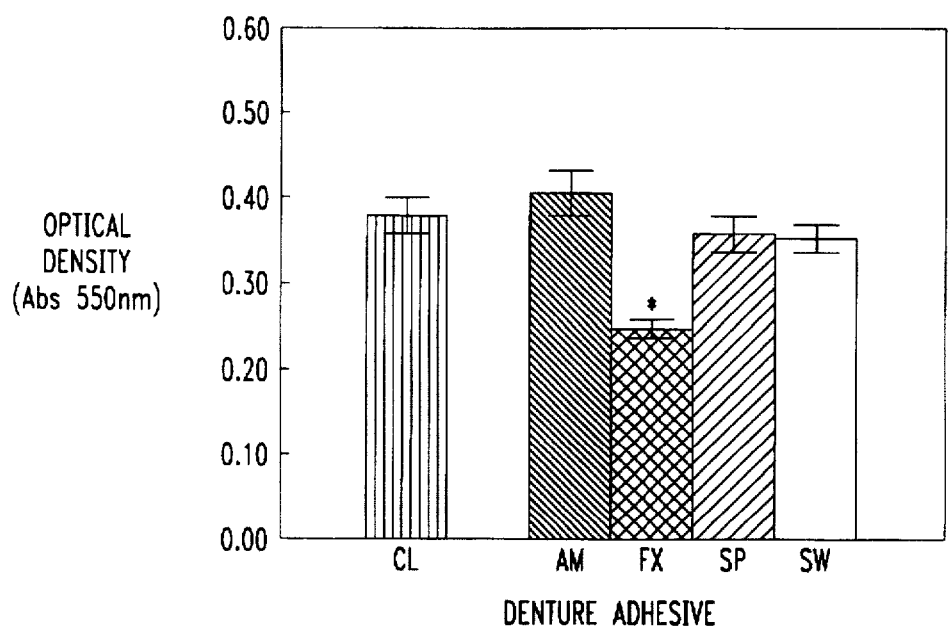
Figure 13:
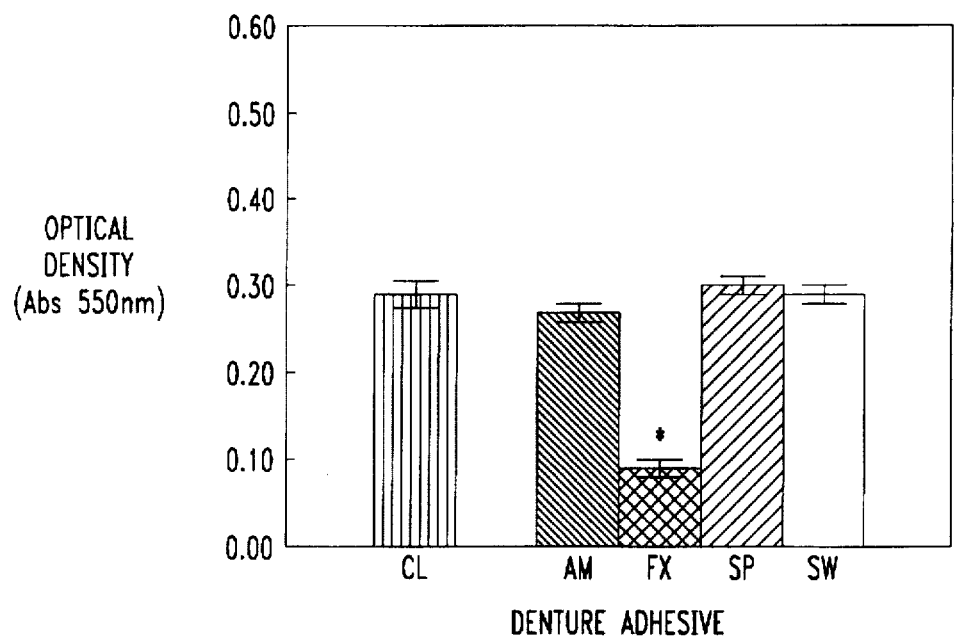
Figure 14:
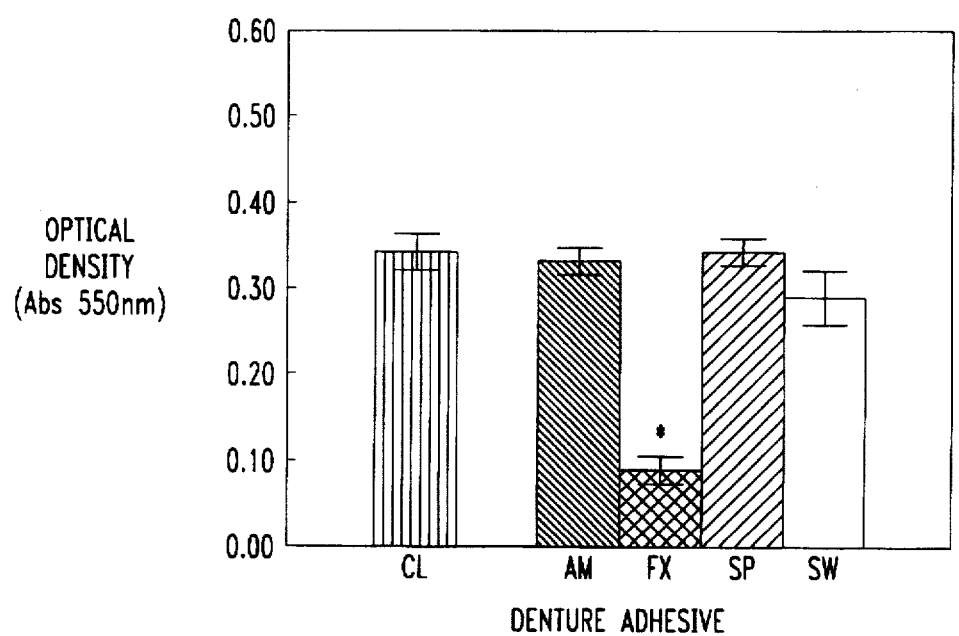

Results of the MTT cytological assay indicated there was no significant difference in optical density (cell viability) between the denture adhesives and the control at the three-hour incubation time (FIG. 11). Following six hours of incubation, Fixodent Fresh exhibited a significantly lower ($P<00.1$) optical density indicating more fibroblast death than the control and all other adhesives (FIG. 12). After the cells were incubated for 12 and 24 hours, Fixodent Fresh continued to demonstrate lower optical densities ($P<0.001$) than the control, Acemannan Wafer, Super Wernet's, and Super Poli Grip (FIGS. 13 and 14, respectively).

In an in vitro adhesive strength test, Aloe Vera Mucilaginous Polysaccharide ("AVMP®") powder tested at zero time wet (water temperature approximately 37 degrees Celsius) was found to posses a mean force of 1.193 lbs. When the same powder was tested dry, the AVMP® powder was found to have a mean force of 1.617 lbs.

Figure 15:
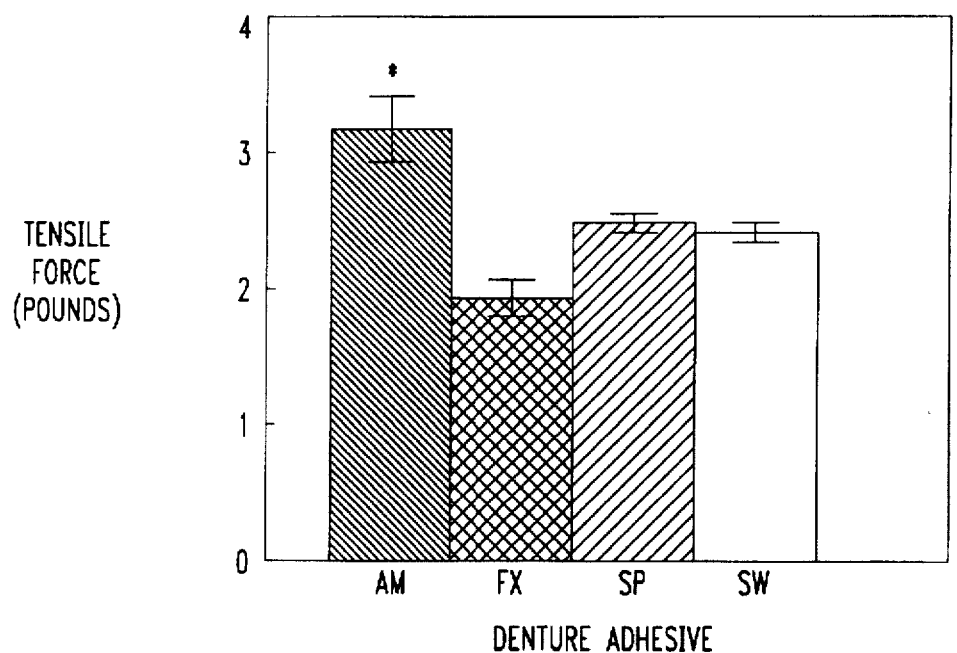
FIG. 15 shows the mean adhesive strength of different denture adhesives.
Figure 16:
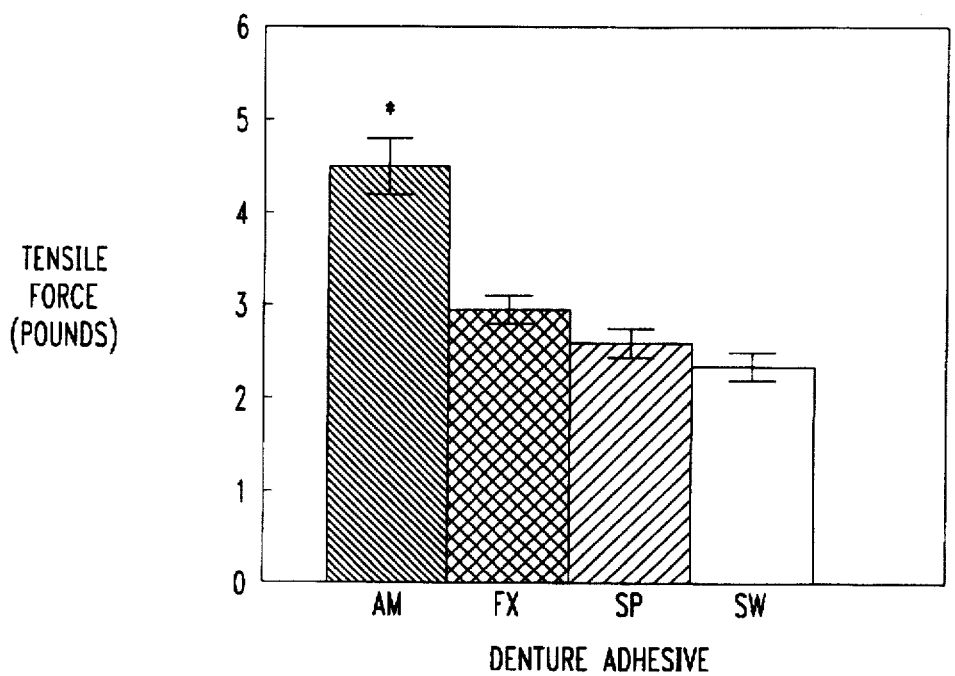
FIG. 16 shows the initial dry strength of different denture adhesives.
Figure 17:
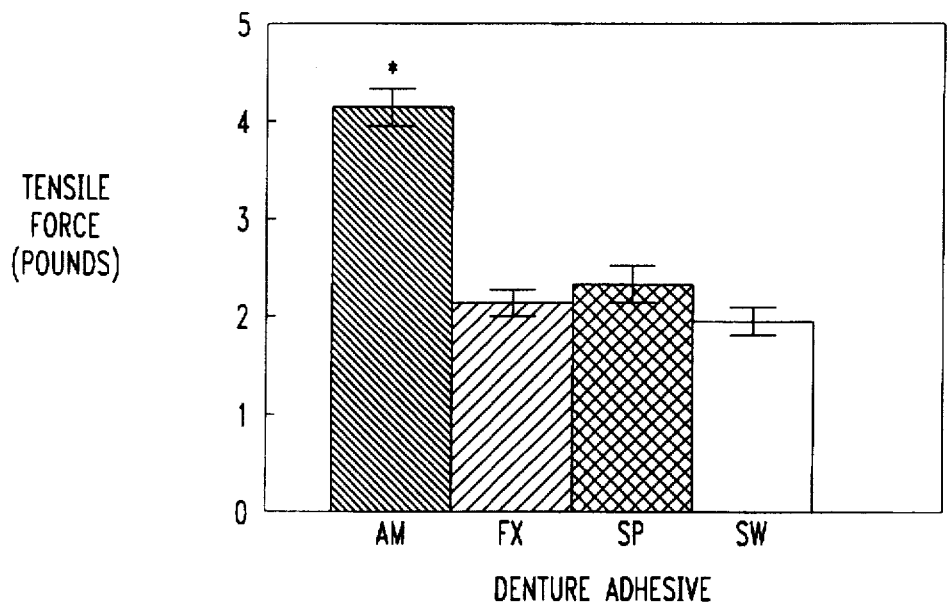
FIGS. 17–22 show the wet strength of different denture adhesives after various time periods. The time period is 0 minute, 3 minutes, 6 minutes, 9 minutes, 15 minutes and 20 minutes for FIGS. 17, 18, 19, 20, 21, and 22, respectively.
Figure 18:
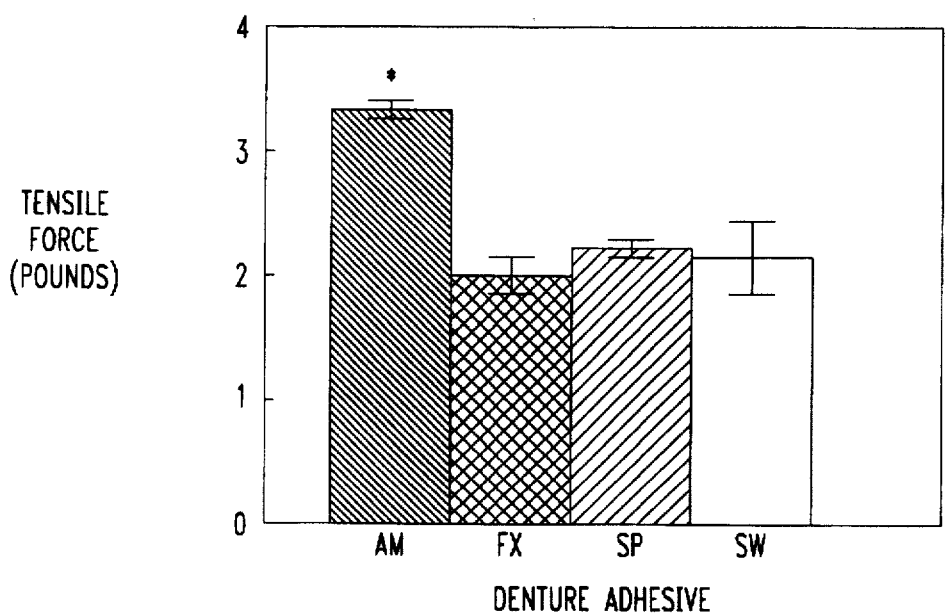
Figure 19:
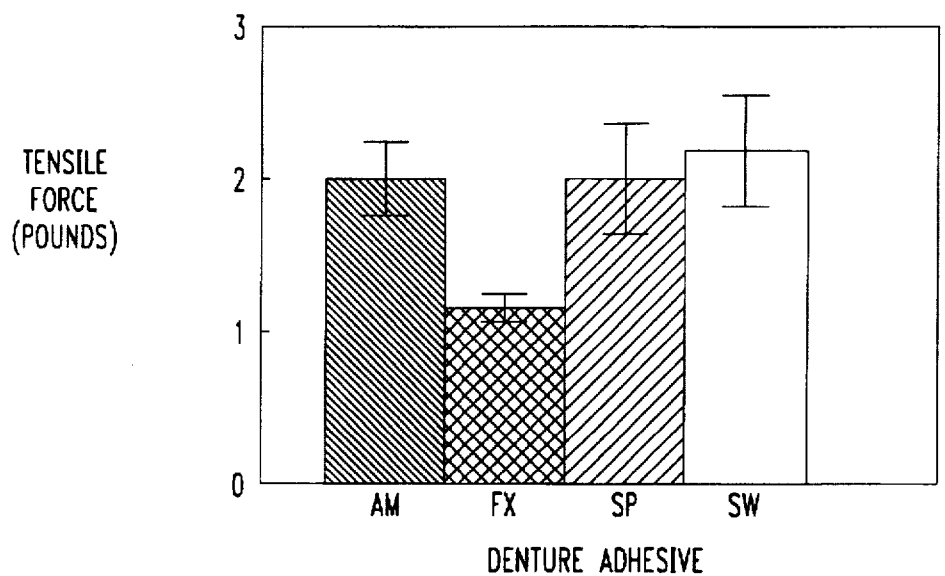
Figure 20:
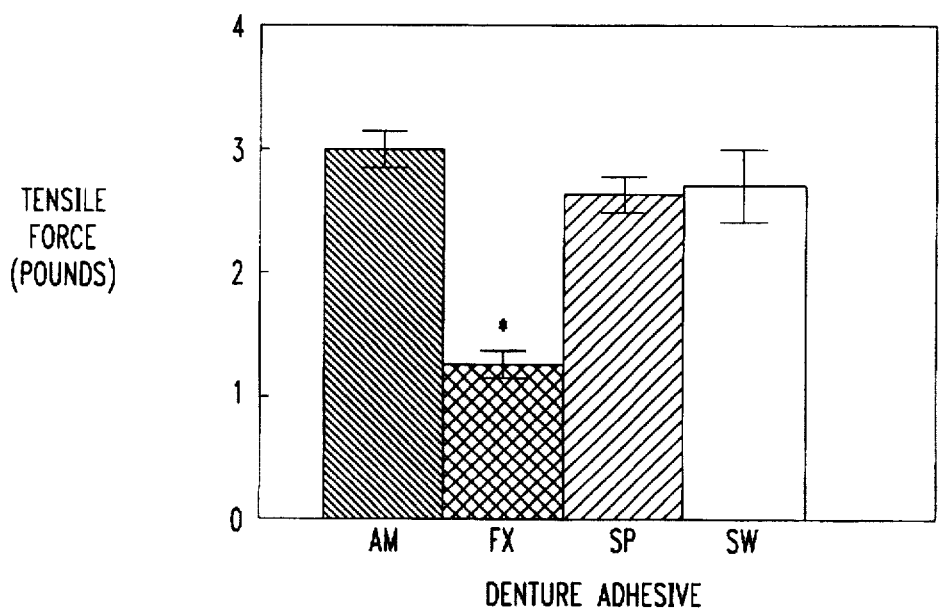
Figure 21:
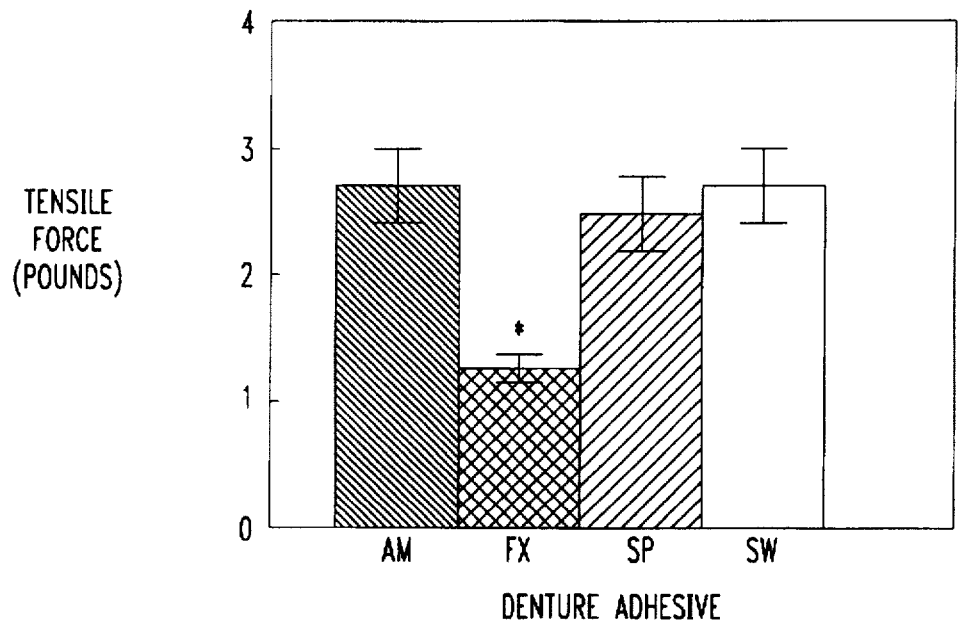
Figure 22:
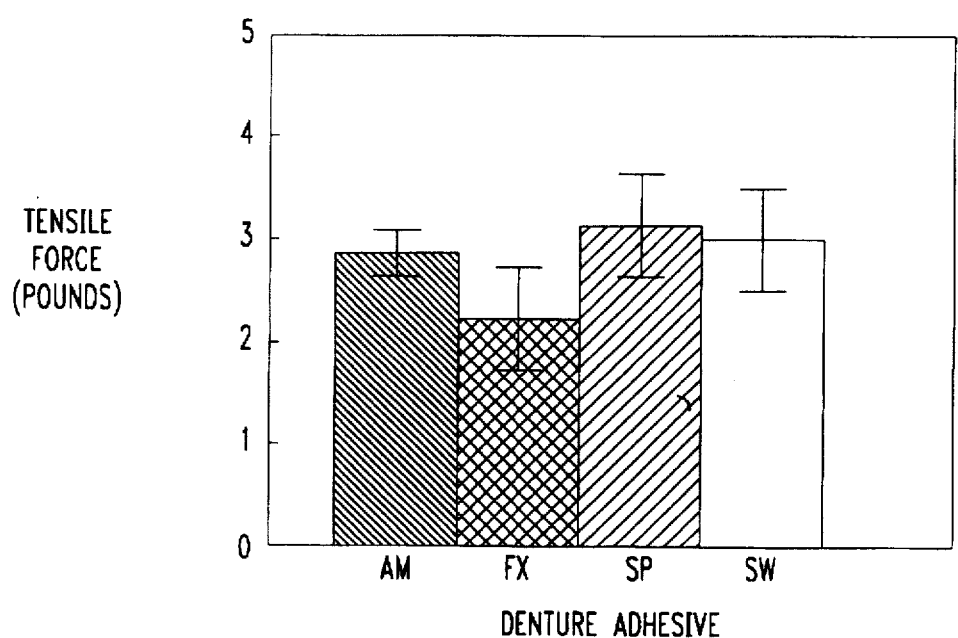

Results of the adhesive strength testing indicated that Acemannan Wafer was the strongest adhesive overall but only significantly stronger than Fixodent Fresh ($P<0.01$). The mean adhesive strengths for the products over the entire test period are illustrated in FIG. 15. At the initial dry placement, Acemannan Wafer was significantly stronger ($P<0.001$) than Super Poli Grip, Super Wernet's and Fixodent Fresh (FIG. 16). Acemannan Wafer was also significantly stronger ($P<0.001$) at the initial (time 0) wet reading and the three minute wet reading than the other adhesives (FIGS. 17 and 18, respectively). The six minute wet time demonstrated no significant difference between products (FIG. 19). At 9 and 15 minutes wet, Fixodent Fresh was significantly weaker ($P<0.01$) than the other adhesives (FIGS. 20 and 21, respectively). At 20 minutes wet, no significant differences were noted between any of the adhesive products (FIG. 22).

The denture adhesives exhibited varied bond failure modes among products but remained consistent over time and were the same in wet versus dry conditions. Super Wernet's debonded adhesively (adhesive failure) with approximately 90% of the material remaining on the acrylic resin cylinder. This material was the most difficult to handle and clean up due to a tenacious slime film residue. The Fixodent Fresh and Super Poh Grip exhibited predominately cohesive bond failures with fairly equal amounts remaining on both the acrylic resin cylinders and the bottom of the bowl. The Fixodent Fresh seemed to have the lower viscosity and film thickness of the two pastes. The Acemannan Wafer exhibited a complete cohesive bond failure and seemed to dissolve in the wet environment into an extremely thin layer which was difficult to visualize but could be felt with a finger on the acrylic resin cylinders or the bottom of the bowl. Clean up was by far the easiest with the Acemannan Wafer and film thickness was considerably thinner than any of the other products.

In another study, the adhesive forces of two denture adhesives, both containing substances isolated or derived from aloe, were determined after being submerged in water at ambient temperature for various time periods. One of the denture adhesive tested was Acemannan Wafer, the other denture adhesive tested was prepared as described in Example 2, Embodiment B. The result of the study is given below:

| Adhesive Forces (lbs.) Of Acemannan Wafer | | | | | | |
|---|---|---|---|---|---|---|
| | Time (minutes) | | | | | |
| Sample | 0 | 3 | 6 | 9 | 15 | 20 |
| 1 | 3.515 | 4.401 | 2.301 | 3.895 | 4.375 | 4.047 |
| 2 | 4.476 | 4.047 | 4.072 | 3.212 | 3.819 | 3.263 |
| 3 | 3.718 | 3.389 | 2.833 | 2.858 | 2.504 | 5.21 |
| 4 | 3.869 | 2.782 | 2.327 | 2.681 | 3.364 | 3.92 |
| 5 | 4.021 | 4.578 | 3.92 | 4.957 | 2.883 | 3.161 |
| Mean | 3.92 | 3.84 | 3.09 | 3.52 | 3.39 | 3.92 |
| Std Dev. | 0.36 | 0.75 | 0.85 | 0.93 | 0.74 | 0.82 |

| Adhesive Forces (lbs.) Of Example 2, Embodiment B | | | | | | |
|---|---|---|---|---|---|---|
| | Time (minutes) | | | | | |
| Sample | 0 | 3 | 6 | 9 | 15 | 20 |
| 1 | 6.045 | 4.906 | 5.615 | 4.881 | 4.52 | 3.895 |
| 2 | 5.286 | 4.755 | 4.198 | 4.552 | 5.008 | 5.159 |
| 3 | 4.755 | 5.438 | 4.957 | 4.502 | 5.918 | 5.488 |
| 4 | 5.893 | 5.235 | 6.727 | 6.879 | 5.21 | 5.792 |
| 5 | 6.07 | 5.26 | 5.817 | 6.323 | 4.603 | 5.589 |
| Mean | 5.61 | 5.12 | 5.46 | 5.43 | 5.05 | 5.18 |
| Std Dev. | 0.57 | 0.28 | 0.95 | 1.10 | 0.58 | 0.76 |

Discussion

All of the denture adhesives tested in this study at some time and dilution exhibited pH values below 5.5 which is considered critical for dissolving hydroxyapatite. Acemannan Wafer and Fixodent Fresh were below pH 6.5 for most of the 24 hours, while Super Wernet's and Super Poli Grip were at or above pH=6.5. This indicates that as far as the present formulations are concerned, the latter two denture adhesives would be more appropriate for partially edentulous patients who may be susceptible to acidic dissolution of enamel (hydroxyapatite). However, the adhesives tested in this study were dissolved in deionized water at percent solutions consistent with expected conditions in the oral cavity as well as previous investigations. W. B. Love, et al., "Denture Adhesive-pH and Buffering Capacity," J. Prosth. Dent., 66:356–360 (1991). Denture adhesives used in vivo would be exposed to dilution and dissolution by saliva which contains many components not present in deionized water. W. B. Love, et al. (ibid.) found Super Wernet's and Super Poli Grip to be highly buffered and resistant to pH changes when exposed to saliva until heavily diluted. This buffering may not be a disadvantage because these denture adhesives never dropped below the critical pH using our experimental conditions. Acemannan Wafer seemed to have no buffering potential due to the lack of any buffers in its ingredients. Accordingly, Acemannan Wafer exhibited the largest pH change from an initial relative acidic condition at placement to a more basic condition over time and eventually exhibited no significant difference compared to the other products once diluted beyond a 2.5% solution. Acemannan Wafer exhibited the lowest mean pH over multiple dilutions. Cytological evaluation of the denture adhesives in our system revealed that none of the products were cytotoxic as compared to the control except Fixodent Fresh. Fixodent Fresh began showing significant cytotoxicity after six hours of exposure to human gingival fibroblasts. The optical densities were considered to be representative of cellular viability because those cells that do not have healthy mitochondria exhibit low succinic dehydrogenase activity as measured by the MTT assay. The assay was assumed to be accurate and reliable because none of the optical densities of the products tested were significantly above the control values. Some differences among the other products did exist but none were significant.

The MTT assay utilized for cytological testing in this study differs from previous investigations which have used an agarose overlay type of test to determine cell death. The MTT assay has the advantage of detection of cell viability and functional activation of cells as a result of the presence of active mitochondrial enzymes whereas agarose overlay tests can count nonactivated or "sick" cells as part of vital cell populations. Examples of preservatives that are potentially cytotoxic include hexachlorophene, sodium tetraborate, sodium borate, and ethanol. Super Wernet's and Super Poli Grip are thought to contain less cytotoxic or smaller amounts of preservatives which would explain their low cytotoxicity. Acemannan Wafer, which was the least cytotoxic of the denture adhesives, contains benzethonium chloride as a preservative and this may be responsible for the minimal cellular death that occurred.

There are no reports that have studied the potential for microbial growth in the aloe vera gel extract when exposed to oral microflora. Its carbohydrate nature, low cytotoxicity, and apparent low level of preservative make dried aloe extract a unique component for a denture adhesive.

Previous studies have demonstrated that the retention values for Fixodent and other similar commercially available denture adhesives reached a maximum and then declined as a function of time. This has been reported in laboratory and in vivo tests. F. Floystrand, et al., "A Method for Testing Denture Adhesives," J. Prosth. Dent., 66:501–504 (1991). From the time of initial exposure to water or saliva, the adhesives are said to absorb water and swell to form a continuous hydrophilic polymer matrix with a subsequent increase in bond strength. Following the attainment of maximum bond strength, the adhesive loses viscosity over time as a result of a dilution effect coupled with the destruction of the polymer matrix. B. Ellis, et al., "The Composition and Rheology of Denture Adhesive," J. Dent., 8:109–118 (1980). However, this investigation seems to indicate that bond strengths of Super Poli Grip, Fixodent Fresh, and Super Wernet's drop initially when exposed to 37° C. deionized water and gradually increase in strength beyond six minutes to a maximum at 20 minutes. One possible reason could be that water, when first introduced to the bonded surfaces, may disrupt established material relationships resulting in a temporary decrease in bond strength. Once water absorption is initiated, the formation of polymer matrices can occur which would gradually increase the strength values.

Acemannan Wafer had the greatest mean bond strength of all adhesives over 20 minutes and was significantly stronger than Fixodent Fresh. Acemannan Wafer becomes a hydrogel when the freeze dried wafer is saturated with water prior to application. It undoubtedly contains a larger proportion of water than the conventional powders and pastes prior to any water absorption after placement. This characteristic may explain its significantly higher initial dry strength, initial wet strength, and 3 minute wet bond strength compared to all the other adhesives.

An important aspect to the success or failure of any denture adhesive is patient acceptance. Patient comfort, ease of use, and clean up are all factors which may influence a patient to select a particular product over another. Patients would enjoy the benefits of superior material consistency, taste, and easy clean up provided by Acemannan Wafer, denture adhesive of this invention. Practically speaking, these factors may override all other considerations if the product becomes available to patients.

An important consideration for dentists is the film thickness of the denture adhesive. Thick films will interfere with the vertical dimension of occlusion. It has been reported that the ideal film thickness for a denture adhesive under complete dentures is 1 mm. D. Benson, et al., "The Effect of A Denture Adhesive on the Oral Mucosa and the Increase in Vertical Dimension of Complete Denture Patients," *J. South. Calif. Dent. Assoc.*, 40:468–473 (1972). Super Poli Grip and Super Wernet's have shown vertical denture displacement values from 0.3 to 0.5 mm with the powder exhibiting smaller displacements. R. Norman, et al., "In Vitro Measurement of Vertical Denture Displacement by Denture Adhesives," Dent. Mater., 3:342–346 (1987). It was found that Acemannan Wafer of this invention consistently provided the most thin and even film thickness of all the denture adhesives.

Intraoral temperature and pH fluctuations combined with muscle movements undoubtedly have some effect on denture adhesive bond strengths. In vitro studies do not necessarily accurately represent these variables. Additionally, the surfaces utilized for in vitro bond strength studies do not necessarily adequately represent the oral mucosa side of the bonding equation. It is highly unlikely that denture adhesives perform in the same manner when bonded to keratinized mucosa as they do when bonded to acrylic resin. In vitro investigations do, however, serve to evaluate and compare currently available and newly developed denture adhesives for the purposes of validating future clinical trials.

Conclusions

With respect to pH, Super Wernet's and Super Poli Grip remained above the critical pH over the 24 hour test period, while Acemannan Wafer, denture adhesive of this invention, and Fixodent Fresh did not. Although there were no significant mean pH differences among products at the 1% and 1.3% dilutions, there were multiple significant differences at varying dilutions for each time interval.

Fixodent Fresh was significantly more cytotoxic than Acemannan Wafer of this invention at six hours (P<0.01) and more cytotoxic than all products tested at 12 and 24 hours (P<0.001).

After being exposed to the wet conditions of this experiment for 20 minutes, there were no significant differences between products. However, there were many significant differences among products for other time intervals. Additionally, the denture adhesive of this invention, Acemannan Wafer, exhibited a significantly higher overall mean bond strength than Fixodent Fresh (P<0.01).

While preferred methods for obtaining and using denture adhesives containing chemical substances isolated and derived from an aloe vera leaf have been disclosed, it will be apparent to those skilled in the art that numerous modifications and variations are possible in light of the above teaching. It should also be realized by those skilled in the art that such modifications and variations do not depart from the spirit and scope of the invention as set forth in the appended claims.

What is claimed is:

1. A method of adhering a denture, having a biocontact surface, to a gum or a roof of a mouth, the method comprising the steps of:
   treating the biocontact surface of the denture with a denture adhesive composition comprising a chemical substance isolated from an aloe gel fillet to obtain a treated denture; and
   placing the treated denture in close proximity to the gum or the roof of the mouth thereby engaging the treated denture with the gum or the roof of the mouth.

2. The method of claim 1, wherein the chemical substance is selected from the group consisting of aloe vera gel extract, bulk acetylated mannan, and acemannan.

3. The method of claim 1, further comprising a dispersant selected from the group consisting of polyvinylpyrrolidone and polyvinylpyrrolidone homopolymer.

4. The method of claim 1, wherein the denture adhesive composition further comprising a thickener.

5. The method of claim 4, wherein the thickener is selected from the group consisting of hydroxyalkylcellulose, alkylcellulose, carboxyalkylcellulose, karaya gum, tragacanth, gelatin, and pectin.

6. The method of claim 4, wherein the thickener is selected from the group consisting of polyethylene oxide, vinyl alkyl ether maleic anhydrides, polyacrylamides, and polyvinyl compound having an acetic acid side chain.

7. A method of adhering a denture, having a biocontact surface, to a gum or a roof of a mouth, the method comprising the steps of:
   treating the biocontact surface of the denture with a denture adhesive composition comprising concentrated gel from aloe to obtain a treated denture; and
   placing the treated denture in close proximity to the gum or the roof of the mouth thereby engaging the treated denture with the gum or the roof of the mouth.

8. The method of claim 7, wherein the concentrated gel from aloe is selected from the group consisting of aloe vera gel extract, bulk acetylated mannan, and acemannan.

9. The method of claim 7, wherein the denture adhesive composition further comprises a dispersant.

10. The method of claim 9, wherein the dispersant is selected from the group consisting of polyvinylpyrrolidone and polyvinylpyrrolidone homopolymer.

11. The method of claim 7, wherein the denture adhesive composition further comprises a thickener.

12. The method of claim 11, wherein the thickener is selected from the group consisting of hydroxyalkylcellulose, alkylcellulose, carboxyalkylcellulose, karaya gum, tragacanth, gelatin, and pectin.

13. The method of claim 11, wherein the thickener is selected from the group consisting of polyethylene oxide, vinyl alkyl ether maleic anhydrides, polyacrylamides, and a polyvinyl compound having an acetic acid side chain.

14. The method of claim 7, wherein the denture adhesive composition further comprises a preservative.

15. The method of claim 14, wherein the preservative is selected from the group consisting of borate salt, benzoate salt, sorbate, paraben and benzethonium halide.

16. A method of adhering a denture, having a biocontact surface, to a gum or a roof of a mouth, the method comprising the steps of:
   treating the biocontact surface of the denture with a denture adhesive composition comprising:
   (i) chemical substances isolated from an aloe gel fillet; and
   (ii) a dispersant to obtain a treated denture; and
   placing the treated denture in close proximity to the gum or the roof of the mouth thereby engaging the treated denture with the gum or the roof of the mouth.

17. The method of claim 16, wherein the concentrated gel from aloe is selected from the group consisting of aloe vera gel extract, aloe raw gel, bulk acetylated mannan, and acemannan.

18. The method of claim 16, wherein the dispersant is selected from the group consisting of polyvinylpyrrolidone and polyvinylpyrrolidone homopolymer.

19. The method of claim 16, wherein the thickener is selected from the group consisting of hydroxyalkylcellulose, alkylcellulose, carboxyalkylcellulose, karaya gum, tragacanth, gelatin, and pectin.

20. The method of claim 15, further comprising a thickener selected from the group consisting of polyethylene oxide, vinyl alkyl ether maleic anhydrides, polyacrylamides, and polyvingyl compound having an acetic acid side chain.

21. The method of claim 16, wherein the denture adhesive composition further comprises a preservative.

22. The method of claim 21, wherein the preservative is selected from the group consisting of borate salt, benzoate salt, sorbate, paraben and benzethonium halide.

23. A method of adhering a denture, having a biocontact surface, to a gum or a roof of a mouth, the method comprising the steps of:
   treating the biocontact surface of the denture with a denture adhesive composition comprising:
      (i) concentrated gel from aloe;
      (ii) a dispersant; and
      (iii) a thickener to obtain a treated denture; and
   placing the treated denture in close proximity to the gum or the roof of the mouth thereby engaging the treated denture with the gum or the roof of the mouth.

24. The method of claim 23, wherein the concentrated gel from aloe is selected from the group consisting of aloe vera gel extract, bulk acetylated mannan, and acemannan.

25. The method of claim 23, wherein the dispersant is selected from the group consisting of polyvinylpyrrolidone and polyvinylpyrrolidone homopolymer.

26. The method of claim 23, wherein the thickener is selected from the group consisting of hydroxyalkylcellulose, alkylcellulose, carboxyalkylcellulose, karaya gum, tragacanth, gelatin, and pectin.

27. The method of claim 23, wherein the thickener is selected from the group consisting of polyethylene oxide, vinyl alkyl ether maleic anhydrides, polyacrylamides, and a polyvinyl compound having an acetic acid side chain.

28. The method of claim 23, wherein the denture adhesive composition further comprises a preservative.

29. The method of claim 23, wherein the preservative is selected from the group consisting of borate salt, benzoate salt, sorbate, paraben and benzethonium halide.

30. A method of adhering a denture, having a biocontact surface, to a gum or a roof of a mouth, the method comprising the steps of:
   treating the biocontact surface of the denture with a denture adhesive composition, the denture adhesive composition being prepared by mixing:
      (i) from about 0.005 weight percent to about 1 weight percent, based on the total weight of the denture adhesive composition, of concentrated gel from aloe;
      (ii) from about 1 weight percent to about 15 weight percent, based on the total weight of the denture adhesive composition, of polyvinylpyrrolidone;
      (iii) from about 2 weight percent to about 15 weight percent, based on the total weight of the denture adhesive composition, of hydroxyalkylcellulose;
      (iv) from about 5 weight percent to about 20 weight percent, based on the total weight of the denture adhesive composition, of about 3% of hydrogen peroxide;
      (v) from about 0.002 weight percent to about 0.5 weight percent, based on the total weight of the denture adhesive composition, of benzethonium chloride; and
      (vi) remainder water to obtain a treated denture;
   placing the treated denture in close proximity to the gum or the roof of the mouth thereby engaging the treated denture with the gum or the roof of the mouth.

31. The method of claim 30, wherein the concentrated gel from aloe is selected from the group consisting of aloe vera gel extract, bulk acetylated mannan, and acemannan.

32. A method of adhering a denture, having a biocontact surface, to a gum or a roof of a mouth, the method comprising the steps of:
   treating the biocontact surface of the denture with a denture adhesive composition, the denture adhesive composition being prepared by mixing:
      (i) from about 0.005 weight percent to about 1 weight percent, based on the total weight of the denture adhesive composition, of concentrated gel from aloe;
      (ii) from about 1 weight percent to about 15 weight percent, based on the total weight of the denture adhesive composition, of polyvinylpyrrolidone;
      (iii) from about 2 weight percent to about 15 weight percent, based on the total weight of the denture adhesive composition, of hydroxyalkylcellulose;
      (iv) from about 0.002 weight percent to about 0.5 weight percent, based on the total weight of the denture adhesive composition, of methyl paraben;
      (v) from about 0.002 weight percent to about 0.5 weight percent, based on the total weight of the denture adhesive composition, of benzethonium chloride;
      (vi) from about 0.05 weight percent to about 0.4 weight percent, based on the total weight of the denture adhesive composition, of a chelating agent;
      (vii) from about 2 weight percent to about 10 weight percent of dilute inorganic base;
      (viii) from about 0.01 weight percent to about 1 weight percent, based on the total weight of the denture adhesive composition, of a sweetener; and
      (ix) remainder water
   placing the treated denture in close proximity to the gum or the roof of the mouth thereby engaging the treated denture with the gum or the roof of the mouth.

33. The method of claim 32, wherein the concentrated gel from aloe is selected from the group consisting of aloe vera gel extract, bulk acetylated mannan, and acemannan.

* * * * *

UNITED STATES PATENT AND TRADEMARK OFFICE
CERTIFICATE OF CORRECTION

PATENT NO. : 5,760,102
DATED : June 2, 1998
INVENTOR(S) : Hall, et al.

It is certified that error appears in the above-indentified patent and that said Letters Patent is hereby corrected as shown below:

Col. 2, line 64 "function" should be --friction--;

Col. 5, line 56 "Wemet" should be --Wernet--;

Col. 6, line 53 "get" should be --gel--;

Col. 14, line 32 "Weinet's" should be --Wernet's--;

Col. 17, line 55 "6.4+0.1" should be --6.4 ± 0.1--;

Col. 18, line 2 "Weniet's" should be --Wernet's--;

Col. 18, line 12 "(P<00.1)" should be --(P<0.01)--; and

Col. 18, line 48 "Poh" should be --Poli--.

Signed and Sealed this

First Day of September, 1998

Attest:

BRUCE LEHMAN

*Attesting Officer*  *Commissioner of Patents and Trademarks*